United States Patent
Tanaka et al.

(10) Patent No.: US 7,774,146 B2
(45) Date of Patent: Aug. 10, 2010

(54) BIOLOGICAL INFORMATION MEASUREMENT DEVICE AND METHOD OF MEASURING BIOLOGICAL INFORMATION SUITABLE FOR REGULAR MEASUREMENT OF BIOLOGICAL INFORMATION

(75) Inventors: Shinya Tanaka, Kyoto (JP); Jiazheng Jin, Kyoto (JP); Yumi Kinoshita, Kyoto (JP); Takeshi Kubo, Katano (JP); Eisuke Yamazaki, Itami (JP)

(73) Assignee: Omron Healthcare Co., Ltd., Kyoto-shi (JP)

(*) Notice: Subject to any disclaimer, the term of this patent is extended or adjusted under 35 U.S.C. 154(b) by 316 days.

(21) Appl. No.: 11/942,423

(22) Filed: Nov. 19, 2007

(65) Prior Publication Data

US 2008/0294348 A1    Nov. 27, 2008

(30) Foreign Application Priority Data

Nov. 20, 2006   (JP)   ............... 2006-312970

(51) Int. Cl.
G06F 19/00 (2006.01)

(52) U.S. Cl. ............... 702/19; 702/21; 600/509; 600/551; 600/300; 705/2; 705/3

(58) Field of Classification Search ............... 702/21, 702/19; 600/509, 551, 300; 705/2, 3
See application file for complete search history.

(56) References Cited

U.S. PATENT DOCUMENTS

| | | | | |
|---|---|---|---|---|
| 6,041,257 A | * | 3/2000 | MacDuff et al. | ............... 607/5 |
| 6,047,207 A | * | 4/2000 | MacDuff et al. | ............ 600/510 |
| 6,558,321 B1 | * | 5/2003 | Burd et al. | ................... 600/300 |
| 2003/0013988 A1 | * | 1/2003 | Kodama et al. | ............. 600/551 |
| 2005/0144042 A1 | * | 6/2005 | Joffe et al. | ..................... 705/2 |
| 2005/0273305 A1 | * | 12/2005 | Thalhammer-Reyero | ..... 703/11 |
| 2006/0217623 A1 | | 9/2006 | Morganroth | |

FOREIGN PATENT DOCUMENTS

| | | |
|---|---|---|
| CN | 1212101 C | 7/2005 |
| EP | 1 275 341 | 1/2003 |
| EP | 1 568 318 | 8/2005 |
| JP | 05-207981 | 8/1993 |
| JP | 2005-073763 | 3/2005 |
| JP | 2006-026210 | 2/2006 |
| WO | WO-2006/032653 | 3/2006 |

OTHER PUBLICATIONS

Chinese Office Action, mailed Feb. 27, 2009, directed to corresponding Chinese Patent Application No. 2007101870401; 11 pages.
European Search Report dated Feb. 22, 2008, directed at counterpart EP application No. 07120912.6; 6 pages.

* cited by examiner

Primary Examiner—Carol S Tsai
(74) Attorney, Agent, or Firm—Morrison & Foerster LLP

(57) ABSTRACT

A biological information measurement device stores, in a storage unit, biological data representing data of calculated biological information and measurement date data in association with each other. The biological information measurement device displays, as measurement frequency specifying information, information for specifying frequency of day(s) when the measurement was conducted, in a prescribed period from a current date based on a plurality of pieces of measurement date data stored in the storage unit and an output from a time keeping unit.

12 Claims, 14 Drawing Sheets

BIOLOGICAL INFORMATION MEASUREMENT DEVICE AND METHOD OF MEASURING BIOLOGICAL INFORMATION SUITABLE FOR REGULAR MEASUREMENT OF BIOLOGICAL INFORMATION

BACKGROUND OF THE INVENTION

1. Field of the Invention

The present invention relates to a biological information measurement device and a method of measuring biological information, and more particularly to a biological information measurement device and a method of measuring biological information suitable for regular measurement of biological information.

2. Description of the Background Art

In a body composition monitor utilizing impedance, for daily management of body composition, it is necessary to conduct measurement in approximately the same time zone every day in order to eliminate influence of circadian rhythm due to an amount of movement of total body water.

In addition, it is indispensable to conduct measurement every day in order to obtain accurate trend information of the body composition. A user whose daily body composition value hardly varies, however, loses motivation to measure body composition and less frequently conducts measurement. Namely, it has been difficult to continue management of body composition.

The following are examples of a conventional biological information measurement device including a body composition monitor. Japanese Patent Laying-Open No. 05-207981 (Paragraphs 0009 and 0052) describes a portable automatic blood pressure monitor including measurement time setting means for setting in advance a next measurement time for a subject in association with an identification number of the subject, in which an alarm is issued and the identification number of the subject is displayed when the time set by the measurement time setting means has come. Forgetting of measurement of blood pressure can thus be avoided and such burden as remembering the time to measure blood pressure can be mitigated.

In addition, Japanese Patent Laying-Open No. 2005-073763 (Paragraph 0009) describes a portable telephone containing a biological sensor, that includes measurement time notification means for notifying a user of the measurement time set in advance, by means of at least one of sound, voice, and vibration. It is thus ensured that the user can know that the measurement time has come, so that data necessary from a medical point of view, i.e., blood glucose level, can be measured at appropriate time and it is expected that forgetting of measurement as in a conventional example is unlikely.

Moreover, Japanese Patent Laying-Open No. 2006-026210 (Paragraphs 0025 and 0079) describes a portable healthcare device with an alarm function for notification of time of measurement of blood pressure and body fat. Thus, this device allows measurement at a predetermined time every day, without forgetting.

According to the devices described in the publications above, though the user is urged to conduct measurement by warning or alarm, the warning or alarm is merely issued when the time of measurement comes, regardless of whether measurement is actually conducted or not. Namely, as there is no change whether measurement is actually conducted or not, it has been difficult to have the user keep motivation.

SUMMARY OF THE INVENTION

The present invention was made to solve the above-described problems, and an object of the present invention is to provide a biological information measurement device and a method of measuring biological information capable of having a subject keep motivation to continue measurement.

In order to achieve the above-described object, according to one aspect of the present invention, a biological information measurement device includes a measurement unit, a first calculation unit, a storage unit, a time keeping unit, a display control unit, and a display unit. The measurement unit senses characteristic information of a subject and converts the characteristic information to a corresponding signal. The first calculation unit calculates biological information of the subject based on the corresponding signal. The storage unit stores biological data representing data of the biological information and measurement date data representing a day on which measurement by the measurement unit was conducted, in association with each other. The time keeping unit performs a time keeping operation. The display control unit carries out control for displaying measurement frequency specifying information based on a plurality of pieces of measurement date data stored in the storage unit and an output from the time keeping unit. The measurement frequency specifying information is information for specifying frequency of day(s) when measurement was conducted, in a prescribed period from current date. The display unit provides display in accordance with an output from the display control unit.

According to the present invention, with the biological information measurement device, the characteristic information of the subject is sensed and converted to the corresponding signal, and the biological information of the subject is calculated based on the corresponding signal. In addition, the biological data representing the data of the calculated biological information and the measurement date data representing the day on which measurement by the measurement unit was conducted are stored in association with each other, and the measurement frequency specifying information for specifying frequency of day(s) when the measurement was conducted, in the prescribed period from the current date, is displayed.

Therefore, with the biological information measurement device, the subject can be notified of the frequency of day(s) when measurement of the biological information was conducted within the prescribed period. Consequently, a biological information measurement device capable of having the subject keep motivation to continue measurement of the biological information in order to obtain accurate trend of the biological information can be provided.

Preferably, the biological information includes at least any of weight and body composition.

Preferably, the storage unit further stores measurement time data of the biological information in association with the biological data and the measurement date data, and the biological information measurement device further includes a second calculation unit calculating next measurement time based on measurement time data stored in the storage unit, and a notification unit performing processing for giving notification that current time is included in a prescribed time zone including the next measurement time calculated by the second calculation unit.

According to the present invention, the biological information as well as the date and measurement time data of the biological information are stored in association with each other, the next measurement time is calculated based on the stored measurement time data, and the notification that the current time is included in the prescribed time zone including the calculated next measurement time is given.

Therefore, with the biological information measurement device, the subject can be notified of the fact that a time zone includes the next measurement time calculated based on the time of measurement. Consequently, the subject can be urged to measure the biological information around the next measurement time based on the time of measurement when the previous measurement was conducted.

Preferably, the prescribed time zone refers to a time zone starting from 0 minutes past X o'clock when the next measurement time is assumed as Y minutes past X o'clock.

According to the present invention, the subject is notified that the current time is included in the time zone starting from 0 minutes past X o'clock.

For example, in an example where the prescribed time zone is assumed as a time zone covering one hour, i.e., including 30 minutes before and after the next measurement time (hereinafter referred to as "a scheduled time of measurement"), if the scheduled time of measurement is 45 minutes past 23 o'clock, the subject is notified from 15 minutes past 23 o'clock until 15 minutes past 0 o'clock that the current time is included in the prescribed time zone. It is assumed that notification is given from 15 minutes past 23 o'clock on the first day until 15 minutes past 0 o'clock on the second day and that the biological information is measured during a period from 15 minutes past 23 o'clock to 59 minutes past 23 o'clock on the first day in response to the notification. In addition, it is assumed that notification is given from 15 minutes past 23 o'clock on the second day until 15 minutes past 0 o'clock on the third day and that the biological information is measured during a period from 0 minutes past 0 o'clock to 15 minutes past 0 o'clock on the third day in response to the notification. Then, such a result is obtained that measurement was not conducted on the second day, despite the fact that the biological information was measured in response to the notification.

Meanwhile, if the scheduled time of measurement is 10 minutes past 0 o'clock, notification that the current time is included in the prescribed time zone is given from 40 minutes past 23 o'clock until 40 minutes past 0 o'clock. Here, it is assumed that notification is given from 40 minutes past 23 o'clock on the first day until 40 minutes past 0 o'clock on the second day and that the biological information is measured during a period from 0 minutes past 0 o'clock to 40 minutes past 0 o'clock on the second day in response to the notification. In addition, it is assumed that notification is given from 40 minutes past 23 o'clock on the second day until 40 minutes past 0 o'clock on the third day and that the biological information is measured during a period from 40 minutes past 23 o'clock to 59 minutes past 23 o'clock on the second day in response to the notification. Then, such a result is obtained that measurement was conducted twice on the second day, despite the fact that the measurement was conducted in response to the notification.

According to the biological information measurement device, however, if the scheduled time of measurement is within a period from 23 o'clock until 0 o'clock, notification is given in a time zone starting from 0 minutes past 23 o'clock, and if the scheduled time of measurement is within a period from 0 o'clock until 1 o'clock, notification is given in a time zone starting from 0 minutes past 0 o'clock, so that notification is not given across midnight. Therefore, such an event that a day when measurement was not conducted is produced or measurement is conducted twice on the same day, despite the fact that measurement was conducted in response to the notification, can be avoided.

Preferably, the notification unit gives notification that the current time is included in the prescribed time zone through blinking of a light-emitting device or display and varies interval of turning on and blinking in accordance with a time from the next measurement time.

According to the present invention, with the biological information measurement device, notification that the current time is included in the prescribed time zone is given through blinking of the light-emitting device or display, and the blinking interval is varied in accordance with the time from the next measurement time.

Therefore, with the biological information measurement device, the subject can be urged to measure the biological information in a recognizable manner. In addition, the subject can be notified of the time from the next measurement time.

Preferably, the storage unit stores the biological data, the measurement date data, and the measurement time data for each subject, and the notification unit gives notification that the current time is included in the prescribed time zone for the subject, using a color of a light-emitting device or a color of display predetermined for each subject.

According to the present invention, with the biological information measurement device, notification that the current time is included in the prescribed time zone for the subject is given by the color of the light-emitting device or the color of display predetermined for each subject.

Therefore, with the biological information measurement device, the subject can be notified to which subject the notification that the current time is included in the prescribed time zone is directed. Consequently, the subject who should conduct measurement can be urged to measure the biological information.

Preferably, the display unit includes a liquid crystal panel, and the display control unit displays the measurement frequency specifying information on the liquid crystal panel by displaying block(s) corresponding to the day(s) on which the measurement was conducted, among a plurality of blocks arranged on a circumference in the number corresponding to the number of days included in the prescribed period, in a display manner distinguishable from other block(s). The biological information measurement device further includes a light-emitting device provided on a back side of the liquid crystal panel and at a position corresponding to a prescribed position surrounded by the plurality of blocks such that light emitted therefrom is transmitted through the liquid crystal panel, and the notification unit gives notification that the current time is included in the prescribed time zone by turning on the light-emitting device and causing the light-emitting device to blink.

According to the present invention, a plurality of blocks arranged on the circumference are displayed in a display manner allowing distinction between the day(s) when measurement was conducted and the day(s) otherwise when measurement was not conducted, so that the plurality of blocks are displayed on the liquid crystal panel as the measurement frequency specifying information. In addition, the light-emitting device provided on the back side of the liquid crystal panel, in the approximate center of the circumference around which the plurality of blocks are arranged, such that light emitted therefrom is transmitted through the liquid crystal panel, is turned on and caused to blink. Thus, notification that the current time is included in the prescribed time zone is given.

Therefore, with the biological information measurement device, the subject can be notified, in a recognizable manner, which day(s) within the prescribed period is the day(s) when measurement was conducted and the day(s) when measurement was not conducted. In addition, with the biological information measurement device, the subject can be urged to conduct measurement of the biological information in a recognizable manner. Consequently, motivation to continue measurement of the biological information can further be improved.

Preferably, the storage unit stores the biological data, the measurement date data, and the measurement time data for each subject, the light-emitting device is a multi-color LED, and the notification unit gives notification that the current time is included in the prescribed time zone for the subject, using a color of the light-emitting device predetermined for each subject.

According to the present invention, with the biological information measurement device, notification that the current time is included in the prescribed time zone for the subject is given by the color of the multi-color LED predetermined for each subject.

Therefore, with the biological information measurement device, the subject can be notified to which subject the notification that the current time is included in the prescribed time zone is directed. Consequently, the subject who should conduct measurement can be urged to conduct measurement of the biological information.

Preferably, the display control unit specifies the number of days on which measurement was conducted within the prescribed period, and displays the measurement frequency specifying information by displaying block(s) in the number corresponding to the number of days on which the measurement was conducted, among a plurality of blocks arranged in the number corresponding to the number of days included in the prescribed period, in a display manner distinguishable from other block(s).

According to the present invention, among a plurality of blocks arranged in the number corresponding to the number of days included in the prescribed period, block(s) in the number corresponding to the number of days when the measurement was conducted within the prescribed period is/are displayed in a display manner indicating that the measurement was conducted and block(s) in the number corresponding to the number of days otherwise, i.e., days when the measurement was not conducted, within the prescribed period, is/are displayed in a display manner indicating that the measurement was not conducted, so that the plurality of blocks are displayed as the measurement frequency specifying information.

Therefore, with the biological information measurement device, the subject can be notified of the number of days when the measurement was conducted and the number of days when the measurement was not conducted within the prescribed period, in a recognizable manner. Consequently, motivation to continue measurement of the biological information can be improved.

Preferably, the display control unit displays the measurement frequency specifying information by displaying block(s) corresponding to the day(s) on which the measurement was conducted, among a plurality of blocks arranged sequentially in correspondence with days, in the number corresponding to the number of days included in the prescribed period, in a display manner distinguishable from other block(s).

According to the present invention, a plurality of blocks arranged sequentially in correspondence with days, in the number corresponding to the number of days included in the prescribed period are displayed in a display manner allowing distinction between the day(s) when the measurement was conducted and the day(s) otherwise when the measurement was not conducted, so that the plurality of blocks are displayed as the measurement frequency specifying information.

Therefore, with the biological information measurement device, the subject can be notified, in a recognizable manner, which day(s) within the prescribed period is the day(s) when the measurement was conducted and the day(s) when the measurement was not conducted. Consequently, motivation to continue measurement of the biological information can be improved.

Preferably, the prescribed period is one week, and the display control unit displays the measurement frequency specifying information by displaying block(s) corresponding to the day(s) on which the measurement was conducted, among seven blocks arranged sequentially in correspondence with seven days of a week included in the prescribed period, in a display manner distinguishable from other block(s).

According to the present invention, seven blocks corresponding to respective days of a week that are arranged in the order of seven days of a week are displayed in a display manner allowing distinction between the day(s) when the measurement was conducted and the day(s) otherwise when the measurement was not conducted, so that the seven blocks are displayed as the measurement frequency specifying information.

Therefore, with the biological information measurement device, the subject can be notified, in a recognizable manner, which day(s) of a week is the day(s) when the measurement was conducted and the day(s) when the measurement was not conducted. Consequently, motivation to continue measurement of the biological information can be improved.

According to another aspect of the present invention, a method of measuring biological information is performed in a biological information measurement device including a storage unit storing data, a display unit displaying data, a measurement unit for measuring biological information, a time keeping unit performing a time keeping operation, and a control unit performing operation processing.

The method of measuring biological information includes the steps of: the control unit causing the storage unit to store biological data representing data of the biological information and measurement date data representing a day on which measurement of the biological information was conducted, in association with each other, each time measurement by the measurement unit is conducted; and the control unit causing the display unit to display measurement frequency specifying information for specifying frequency of day(s) when measurement was conducted, in a prescribed period from current date, based on a plurality of pieces of measurement date data stored in the storage unit and an output from the time keeping unit.

According to the present invention, a method of measuring biological information capable of having a subject keep motivation to continue measurement of the biological information in order to obtain accurate trend of the biological information can be provided.

The foregoing and other objects, features, aspects and advantages of the present invention will become more appar-

DESCRIPTION OF THE PREFERRED EMBODIMENTS

Figure 1:
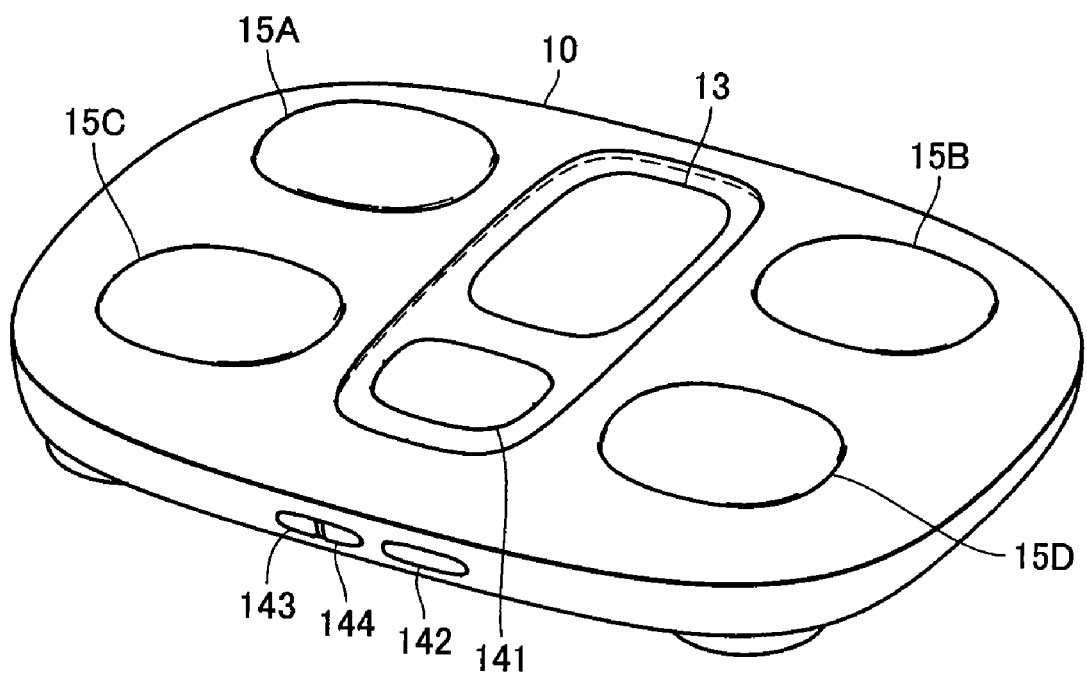
FIG. 1 shows appearance of a body composition monitor with scale in an embodiment of the present invention.

An embodiment of the present invention will be described hereinafter in detail with reference to the drawings. The same or corresponding elements in the drawings have the same reference characters allotted, and description thereof will not be repeated.

FIG. 1 shows appearance of a body composition monitor with scale 10 in an embodiment of the present invention. Referring to FIG. 1, body composition monitor with scale 10 includes a display unit 13, an ON switch 141, an OFF switch 142, a memory switch 143, a guest switch 144, current application electrodes 15A and 15B, and voltage measurement electrodes 15C and 15D.

In addition, as will be described in connection with FIG. 4 later, body composition monitor with scale 10 contains a weight measurement unit 151, a CPU (Central Processing Unit) 110, various circuits, a power supply unit 170, and the like.

Current application electrodes 15A and 15B are arranged on an upper surface of body composition monitor with scale 10 such that toe sides of soles of left and right feet are in contact with these electrodes when a subject gets on body composition monitor with scale 10, respectively. Voltage measurement electrodes 15C and 15D are arranged on the upper surface of body composition monitor with scale 10 such that heel sides of soles of left and right feet are in contact with these electrodes when the subject gets on body composition monitor with scale 10, respectively.

It is noted that current application electrodes 15A and 15B may be arranged on the heel side and voltage measurement electrodes 15C and 15D may be arranged on the toe side.

Display unit 13 is arranged on the upper surface of body composition monitor with scale 10 between current application electrodes 15A and 15B, so that subject's viewability is enhanced in both cases of before the subject gets on body composition monitor with scale 10 and while the subject is standing on body composition monitor with scale 10.

ON switch 141 is arranged on the upper surface of body composition monitor with scale 10 between voltage measurement electrodes 15C and 15D, so that operability of ON switch 141 is enhanced. While the subject is standing on body composition monitor with scale 10, operation of ON switch 141 is inactivated, so that erroneous operation during measurement can be prevented.

OFF switch 142, memory switch 143 and guest switch 144 are arranged on a side surface of body composition monitor with scale 10, on a side where ON switch 141 is arranged, so that erroneous operation during measurement can be prevented.

Figure 2:
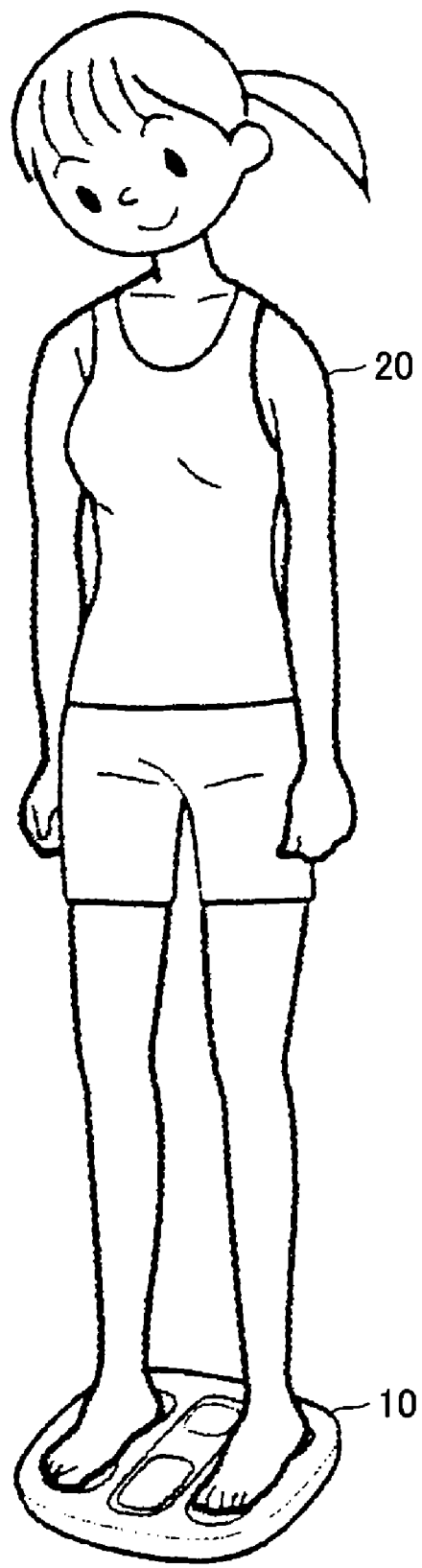
FIG. 2 illustrates a measurement state when a subject measures body composition and weight using the body composition monitor with scale in the present embodiment.

FIG. 2 illustrates a measurement state when subject 20 measures body composition and weight using body composition monitor with scale 10 in the present embodiment. Referring to FIG. 2, in measuring body composition and weight, subject 20 gets on the upper surface of body composition monitor with scale 10 in an erect posture, such that toe sides of soles of left and right feet are in contact with current application electrodes 15A and 15B respectively and heel sides thereof are in contact with voltage measurement electrodes 15C and 15D respectively.

Figure 3:
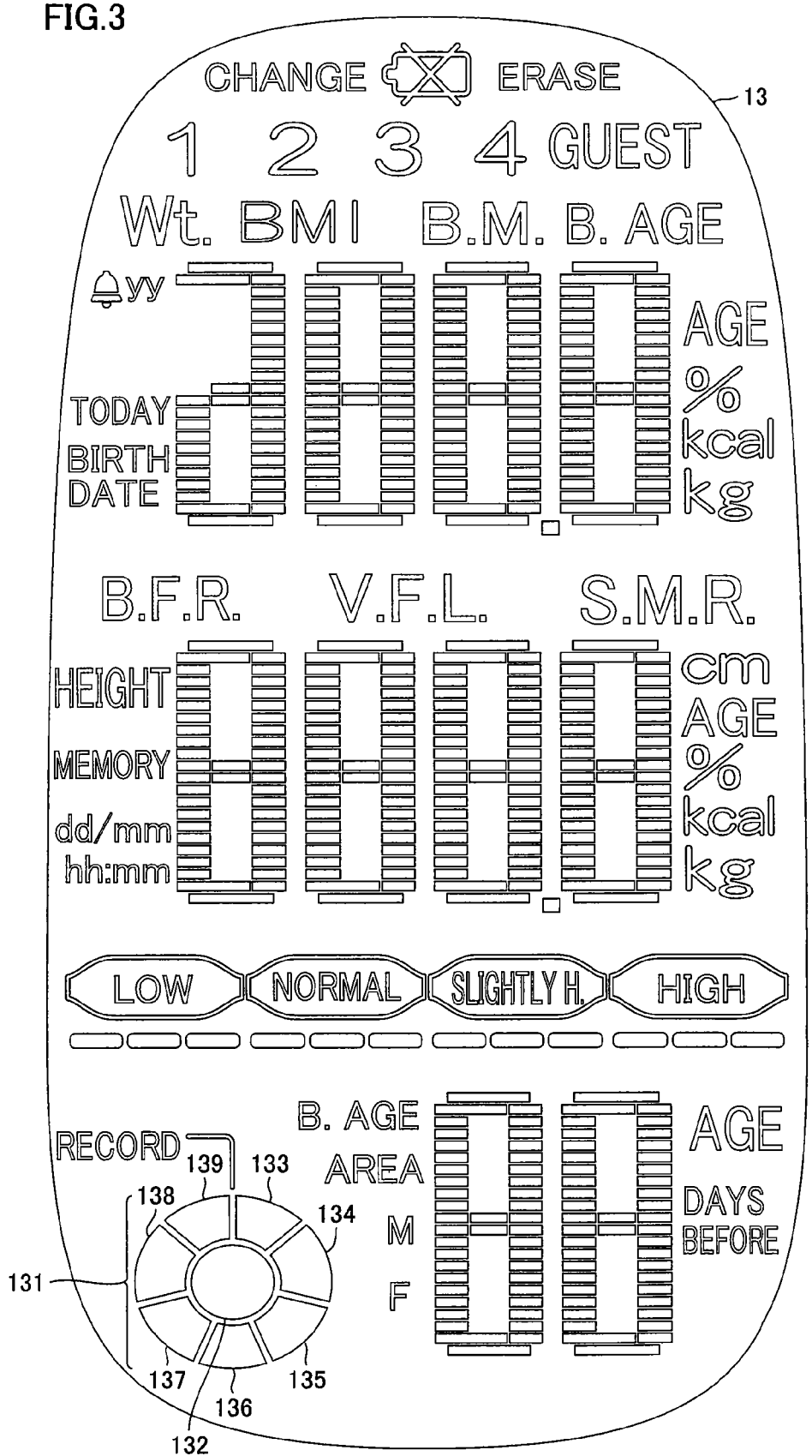
FIG. 3 illustrates a display pattern on a display unit of the body composition monitor with scale in the present embodiment.

FIG. 3 illustrates a display pattern on display unit 13 of body composition monitor with scale 10 in the present embodiment. Referring to FIG. 3, display unit 13 is implemented by a segment-type LCD (Liquid Crystal Display). Therefore, display unit 13 can display a predetermined display pattern.

In the uppermost row of the display pattern of display unit 13, a display pattern of characters of "change", a pictogram "cross mark on battery," and characters "erase" are arranged from the left. "Change" and "erase" are turned on when registered personal data is changed and erased. The "cross mark on battery" is turned on when a battery low state is indicated.

In the second row, a display pattern of characters of "1", "2", "3", "4", and "guest" is arranged from the left. Each of numbers "1", "2", "3", and "4" indicates a personal number for a subject that is associated with data displayed on display unit 13 and a personal number of a subject who is going to conduct measurement. "Guest" represents a guest function and it is turned on when weight and body composition are measured.

In the third row, a display pattern of characters of "weight (Wt.)", "BMI", "basal metabolism (B.M.)", and "body age (B. AGE)" is arranged.

In the fourth row, segments for displaying a part of numbers up to four digits or alphabet are arranged. In addition, a display pattern of characters of "year (yy)", "today", and "date of birth (BIRTH DATE)" showing a type of data that is being displayed and a pictogram of a "bell" is arranged on the left of the segments of four digits, and a display pattern of characters of "age", "%", "kcal", and "kg" showing a unit of data that is being displayed is arranged on the right of the segments of four digits.

"Weight" in the third row and "kg" in the fourth row are turned on while weight is being measured and when data displayed with the segments in the fourth row relates to the weight. "BMI" in the third row is turned on when the data displayed with the segments in the fourth row relates to BMI (Body Mass Index). "Basal metabolism" in the third row and "kcal" in the fourth row are turned on when the data displayed with the segments in the fourth row relates to the basal metabolism.

In the fifth row, a display pattern of characters of "body fat rate (B.F.R.)," "visceral fat level (V.F.L.)" and "skeletal muscle rate (S.M.R.)" is arranged.

In the sixth row, segments for displaying a part of numbers up to four digits or alphabet are arranged. In addition, a display pattern of characters of "height", "memory", "date and month (dd/mm)," and "hours and minutes (hh:mm)" showing a type of data that is being displayed is arranged on the left of the segments of four digits, and a display pattern of characters of "cm", "age", "%", "kcal", and "kg" showing a unit of data that is being displayed is arranged on the right of the segments of four digits.

In the seventh row, a display pattern of characters of "low", "normal", "slightly high (SLIGHTLY H.)", and "high" and boxes around the characters is arranged. In addition, a display pattern of a pictogram representing a determined level is arranged.

"Body fat rate" in the fifth row, "%" in the sixth row, and the characters and the boxes in the seventh row are turned on when data displayed with the segments in the sixth row and the determined level displayed by the pictogram in the seventh row relate to the body fat rate.

"Visceral fat level" in the fifth row and the characters and the boxes in the seventh row are turned on when data displayed with the segments in the sixth row and the determined level displayed by the pictogram in the seventh row relate to the visceral fat level.

"Skeletal muscle rate" in the fifth row, "%" in the sixth row, and the characters and the boxes in the seventh row are turned on when data displayed with the segments in the sixth row and the determined level displayed by the pictogram in the seventh row relate to the skeletal muscle rate.

The "bell" in the fourth row is turned on when activation or inactivation of a notification function, which will be described later, is set. When the notification function is set to active, "on" is displayed with the segments in the fourth row, and when it is set to inactive, "off" is displayed.

"Year" in the fourth row is turned on when the year of birth is set or when the year as of today is set. Here, the year displayed with the segments in the fourth row is changed and set in response to the operation by subject 20.

"Date and month" in the sixth row is turned on when the date and month of birth is set or when the date and month as of today is set. Here, the date and month displayed with the segments in the sixth row is changed and set in response to the operation by subject 20.

"Hours and minutes" in the sixth row is turned on when the current time is set. Here, the hours and minutes displayed with the segments in the sixth row is changed and set in response to the operation by subject 20.

"Date of birth" in the fourth row is turned on when the date of birth is set. Here, the year displayed with the segments in the fourth row or the date and month displayed with the segments in the sixth row is changed and the date of birth is thus set, in response to the operation by subject 20.

"Height" and "cm" in the sixth row are turned on when the height is set. Here, the data displayed with the segments in the sixth row is changed and the height is set, in response to the operation by subject 20.

In the eighth row, a display pattern of characters of "measurement record (RECORD)", a display pattern of a pictogram of a "ring mark 131" indicating frequency of measurement, a display pattern of characters of "body age (B. AGE)", "area", "male (M)", and "female (F)", segments for displaying numbers up to two digits or a part of alphabet, and a display pattern of characters of "age" and "days before" are arranged from the left. Display of "measurement record" and "ring mark 131" in the eighth row will be described later.

"Body age" and "age" in the eighth row are turned on when the data displayed with the segments in the fourth, sixth and eighth rows relates to the body age.

The "area" in the eighth row is turned on when an area number is set. Here, the area number displayed with the segments in the eighth row is changed and set in response to the operation by subject 20. The area number is a number set in order to correct influence by acceleration of gravity, for accurate measurement of weight. When the area is to the north of a prescribed latitude, "1" is set, and when the area is to the south thereof, "2" is set.

"Male" and "female" in the eighth row are turned on when sex is set. Here, switching between "male" and "female" is made in response to the operation by subject 20 and the sex is thus set.

"Days before" in the eight row is turned on when the data displayed with the segments in the sixth row and a determined level displayed by the pictogram in the seventh row indicate the data and the pictogram of certain day(s) before, respectively, the number of which is displayed with the segments in the eighth row.

Figure 4:
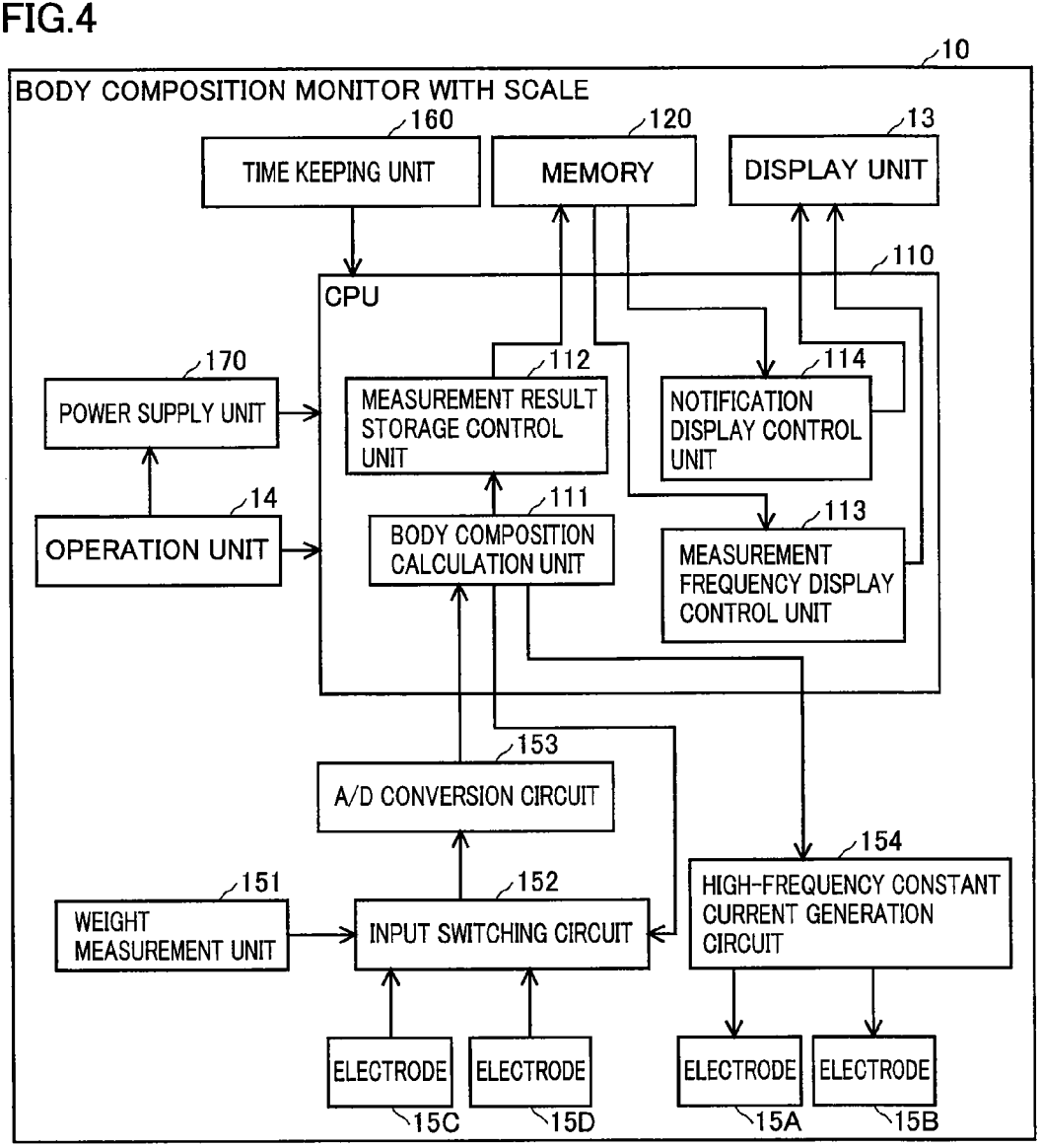
FIG. 4 is a block diagram showing a configuration of the body composition monitor with scale in the present embodiment.

FIG. 4 is a block diagram showing a configuration of body composition monitor with scale 10 in the present embodiment. Referring to FIG. 4, body composition monitor with scale 10 includes current application electrodes 15A and 15B, voltage measurement electrodes 15C and 15D, and display unit 13, as described previously.

In addition, body composition monitor with scale 10 includes CPU 110, an operation unit 14, a high-frequency constant current generation circuit 154, an input switching circuit 152, an A/D (Analog/Digital) conversion circuit 153, power supply unit 170, a memory 120, and a time keeping unit 160.

Operation unit 14 includes ON switch 141, OFF switch 142, memory switch 143, and guest switch 144 described previously.

CPU 110 includes an internal memory, and carries out operation of data and control of each unit in body composition monitor with scale 10 in accordance with a program stored in the internal memory, using the internal memory as a work area.

High-frequency constant current generation circuit 154 generates a high-frequency constant current at a prescribed frequency and feeds the high-frequency constant current to subject 20 in contact with current application electrodes 15A and 15B.

A difference in potential is produced between voltage measurement electrodes 15C and 15D as a result of flow of the high-frequency constant current from current application electrodes 15A and 15B to subject 20. Weight measurement unit 151 is configured by a load cell and used to measure the weight of subject 20.

Input switching circuit 152 switches input to any one of voltage information based on the difference in potential obtained from voltage measurement electrodes 15C and 15D and weight information obtained from weight measurement unit 151. A/D conversion circuit 153 converts the voltage information and the weight information obtained from input switching circuit 152 from an analog signal to a digital signal.

Power supply unit 170 supplies power to each unit in CPU 110 or body composition monitor with scale 10 in response to the operation of ON switch 141 included in operation unit 14. Time keeping unit 160 keeps date and time.

Memory 120 stores information such as measurement result. In the present embodiment, memory 120 includes, for example, an EEPROM (Electrically Erasable Programmable Read-Only Memory), which stores therein personal data of the subject, date or time of measurement, and result of measurement such as body composition or weight, which will be described later.

TABLE 1

| Personal No. | Notification Function | Height | Sex | Year of Birth | Month of Birth | Date of Birth |
|---|---|---|---|---|---|---|
| 1 | on | 169.7 | male | 1970 | 11 | 22 |
| 2 | off | 140.2 | female | 1995 | 8 | 4 |
| 3 | on | 160.5 | female | 1969 | 3 | 10 |
| 4 | — | — | — | — | — | — |

Table 1 shows a storage state of personal data stored in memory 120. Referring to Table 1, as personal data, activation or inactivation of the notification function, height, sex, year of birth, month of birth, and date of birth are set in advance by subject 20 for each personal number of subject 20 and stored in memory 120.

For example, as to a subject having a personal number 1 allotted, memory 120 stores such a state that the notification function is set to "active (on)", height is "169.7"cm, sex is "male", year of birth is "1970", month of birth is "11", and date of birth is "22".

Similarly, as to subjects having personal numbers 2 and 3 allotted respectively, memory 120 stores such states that the notification function is set to "inactive (off)" and "active (on)", height is "140.2"cm and "160.5"cm, sex is "female" and "female", year of birth is "1995" and "1969", month of birth is "8" and "3", and date of birth is "4" and "10", respectively. It is noted that personal data for a subject having a personal number 4 allotted is not stored in memory 120.

Here, in the present embodiment, the personal data includes body-specifying information necessary for calculating body composition of subject 20. The body-specifying information includes at least height and weight of subject 20, and more preferably, the body-specifying information includes age and sex in addition to the height and weight. In the present embodiment, personal data includes height, weight, sex, and year, month and date of birth for calculating age.

In body composition monitor with scale 10, weight measurement unit 151 can measure the weight out of body-specifying information. Therefore, for measurement of body composition, other three types of data (height, sex, and year, month and date of birth for calculating age) are input in advance by subject 20 by means of operation unit 14.

It is noted that body composition monitor with scale 10 may be configured without weight measurement unit 151. In such a case, it is assumed that four items representing the body-specifying information (height, weight, age, and sex) are input in advance by means of operation unit 14.

CPU 110 includes a body composition calculation unit 111, a measurement result storage control unit 112, a measurement frequency display control unit 113, and a notification display control unit 114.

It is noted that body composition calculation unit 111, measurement result storage control unit 112, measurement frequency display control unit 113, and notification display control unit 114 may be configured in CPU 110 as a result of execution by CPU 110 of main processing, measurement processing and notification processing described in connection with FIGS. 6, 7 and 10 respectively, or may be configured as hardware circuits.

Body composition calculation unit 111 calculates biological information, i.e., weight and body composition of the subject, based on the voltage information and the weight information obtained from A/D conversion circuit 153.

Specifically, body composition calculation unit 111 initially calculates the weight based on the weight information. Then, body composition calculation unit 111 controls high-frequency constant current generation circuit 154 to feed the high-frequency constant current from current application electrodes 15A and 15B to subject 20. Body composition calculation unit 111 controls input switching circuit 152 to switch the input to A/D conversion circuit 153 to the voltage information based on the difference in potential from voltage measurement electrodes 15C and 15D. Then, impedance is measured based on the current value of the high-frequency constant current generated by high-frequency constant current generation circuit 154 and the voltage information based on the difference in potential between two electrodes obtained from A/D conversion circuit 153.

Thereafter, body composition calculation unit 111 calculates the body composition of subject 20 based on the height, age and sex set in advance, the calculated weight, and the measured impedance. The body composition refers to the biological information including body fat rate, BMI, visceral fat level, basal metabolism, skeletal muscle rate, body age, and the like. The body composition can be calculated with a known method.

Measurement result storage control unit 112 causes memory 120 to store the time of measurement, the biological information calculated by body composition calculation unit 111, and the date of measurement on which the biological information was calculated, in association with each other. It is noted that the date of measurement refers to a date on which impedance corresponding to the biological information was measured. In the present embodiment, the time of measurement refers to the time at which power of body composition monitor with scale 10 is turned on, for example. The time of measurement serves as a reference time for the "notification" function which will be described later.

TABLE 2

| Number of Days | Date of Measurement | Time of Measurement | Weight | Body Fat Rate | BMI | Visceral Fat Level | Basal Metabolism | Skeletal Muscle Rate | Body Age |
|---|---|---|---|---|---|---|---|---|---|
| 0 | 11/22 | 21:34 | 52.3 | 23.0 | 20.3 | 3 | 1254 | 30.9 | 29 |
| 1 | 11/21 | — | — | — | — | — | — | — | — |
| 2 | 11/20 | 20:57 | 53.1 | 23.6 | 20.7 | 4 | 1263 | 30.2 | 30 |
| 3 | 11/19 | — | — | — | — | — | — | — | — |
| 4 | 11/18 | 22:22 | 53.9 | 24.2 | 21.1 | 5 | 1272 | 29.5 | 31 |
| 5 | 11/17 | — | — | — | — | — | — | — | — |
| 6 | 11/16 | — | — | — | — | — | — | — | — |
| . | . | . | . | . | . | . | . | . | . |
| . | . | . | . | . | . | . | . | . | . |
| 97 | 8/17 | 23:45 | 54.7 | 24.8 | 21.5 | 6 | 1281 | 28.8 | 32 |

Table 2 shows a storage state of biological information stored in memory 120. Referring to Table 2, measurement result storage control unit 112 causes memory 120 to store, in a storage area corresponding to the number of days of "0" that serves as a storage area for storing results of measurement this time, the date of measurement of "November 22", the time of measurement of "21:34", the weight of "52.3" kg, the body fat rate of "23.0" %, the BMI of "20.3", the visceral fat level of "3", the basal metabolism of "1254" kcal, the skeletal muscle rate of "30.9" %, and the body age of "29".

Here, the field of the number of days shows that how many day(s) before the result of measurement was obtained. Specifically, the result of measurement with the number of days of "0" shows the result of measurement of 0 days before, that is, today, while the result of measurement with the number of days of "97" shows the result of measurement 97 days before. Here, any one of the field of the number of days and the field of the date of measurement may be provided. If the field of the date of measurement is solely provided, the date of measurement can be specified from the data in the field of the date of measurement. If the field of the number of days is solely provided, the date of measurement can be specified from the data in the field of the number of days.

When the result of measurement of today is stored for the first time today, the biological information in the storage area corresponding to the number of days of "0" is moved to a storage area corresponding to the number of days of "1" and stored therein. Similarly, the biological information in storage areas corresponding to the number of days of "1" through "96" is moved to storage areas corresponding to the number of days of "2" through "97" and stored therein, respectively.

It is noted that the time of measurement and the biological information in the storage area corresponding to the number of days of "97" are erased from memory 120. When the result of measurement of today is stored a plurality of times, the latest result of measurement may overwrite the previous result in the storage area corresponding to the number of days of "0".

Here, data showing how many days before the result of measurement was obtained is stored as information showing date of measurement, however, the present invention is not limited as such, and data showing the date of measurement itself may be stored.

Measurement frequency display control unit 113 controls display unit 13 to display ring mark 131 serving to specify frequency of day(s) when measurement was conducted that is stored in memory 120, among seven days in a week including today.

Ring mark 131 is displayed such that it is visible from eye level of subject 20 in an erect posture during measurement. Thus, ring mark 131 can be recognized without bringing closer the eyes of subject 20 to display unit 13, so that motivation for measurement can further be enhanced.

Figure 5A:
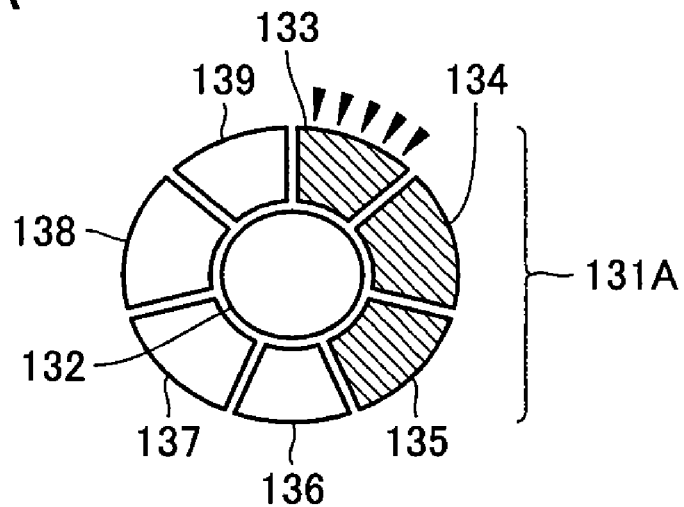
FIGS. 5A to 5C illustrate a ring mark displayed on the display unit of the body composition monitor with scale in the present embodiment.
Figure 5B:
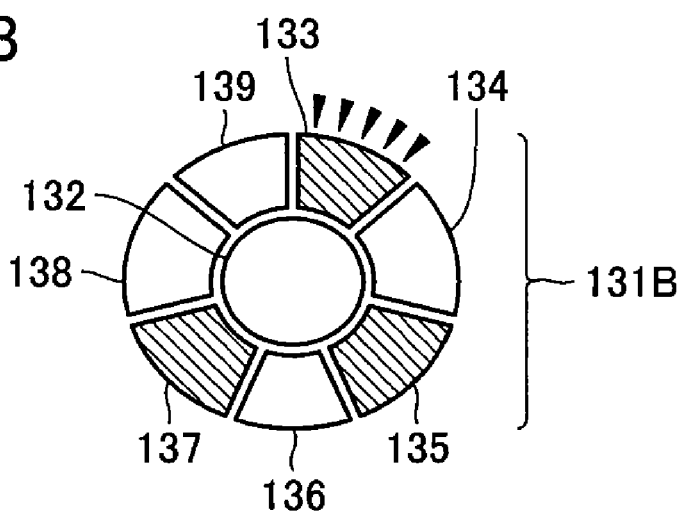
Figure 5C:
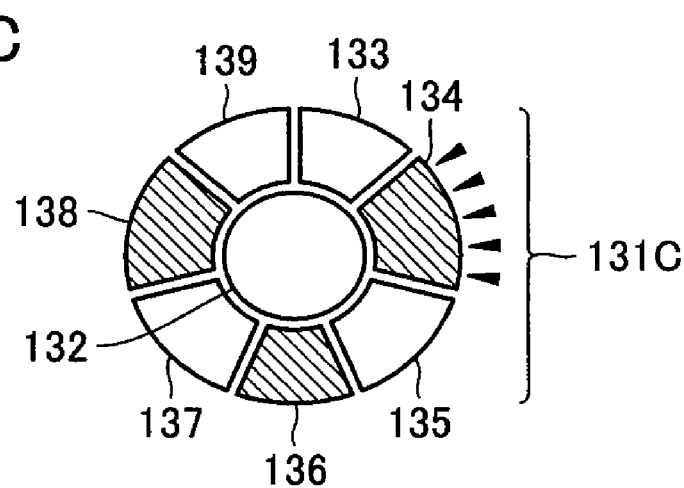

FIGS. 5A to 5C illustrate ring mark 131 displayed on display unit 13 of body composition monitor with scale 10 in the present embodiment. Referring to FIG. 5A, ring mark 131 includes blocks 133 to 139 arranged on a circumference. Blocks 133 to 139 correspond to seven days from today to six days before, respectively. Specifically, measurement frequency display control unit 113 specifies the number of days when measurement was conducted within a period of seven days from today to six days before, and turns on block(s) in the number corresponding to the specified number of days.

For example, as shown in Table 2, in a week including today, if measurement was conducted on three days including today, blocks 134 and 135 in a ring mark 131A corresponding to two days except for today out of the three days are turned on. Block 133 corresponding to today among the three days blinks, in order to show that measurement for today will now be conducted.

In addition, a color display portion 132 for each personal number (hereinafter referred to as personal number color 132) refers to a portion where a color is displayed as a result of transmission of light emitted by a three-color LED provided on the back side of the approximate center of a circle, around which blocks 133 to 139 forming ring mark 131 on display unit 13 implemented as a segment-type LCD as described previously are arranged.

It is noted that the segment-type LCD includes, for example, a liquid crystal panel and an edge-light-type backlight unit. The backlight unit includes a diffusion sheet, a light guide plate and a reflection sheet (a sheet for reflecting light from a fluorescent lamp provided at a side portion), sequentially from the liquid crystal panel side. In the diffusion sheet, the light guide plate and the reflection sheet, a hole is provided at a position corresponding to a position where personal number color 132 is arranged, and the three-color LED is arranged at that hole portion.

The three-color LED is controlled so as to emit light in a color different for each personal number of the subject whose measurement frequency has been shown by ring mark 131. For example, for personal numbers 1 to 4, green, light blue, orange, and pink are allotted respectively. Such allotment of color facilitates identification even by a person having abnormal color sense.

It is noted that any display serving to specify frequency of day(s) when measurement was conducted, among days included in a prescribed period, may be adopted, without limited to display as shown in FIG. 5A.

Specifically, referring to FIG. 5B, measurement frequency display control unit 113 may turn on block(s) arranged on the circumference, corresponding to day(s) when measurement was conducted within a period from today to six days before.

For example, as shown in Table 2, if the days when measurement was conducted include today, two days before and four days before within the period from today to six days before, blocks 135 and 137 corresponding to two days before and four days before in a ring mark 131B are turned on. Block 133 corresponding to today is caused to blink in order to show that measurement for today will now be conducted.

Alternatively, referring to FIG. 5C, blocks 133 to 139 arranged on the circumference are allotted to Monday through Sunday respectively, and measurement frequency display control unit 113 may turn on block(s) allotted to day(s) corresponding to the day(s) when measurement was conducted within the period from today to six days before.

For example, as shown in Table 2, if days when measurement was conducted include today (Tuesday), two days before (Thursday) and four days before (Saturday) in the period from today to six days before, block 136 allotted to Thursday and block 138 allotted to Saturday in a ring mark 131C are turned on. Block 134 allotted to Tuesday corresponding to today is caused to blink in order to show that measurement for today will now be conducted.

Referring back to FIG. 4, while the power is turned off, notification display control unit 114 controls display unit 13 so that subject 20 is notified through personal number color 132 that the current time is included in a measurement time zone during which subject 20 should measure the biological information. Namely, notification display control unit 114 gives "notification". In the present embodiment, the measurement time zone refers to a time zone including, for duration of one hour, thirty minutes before and after the time of previous measurement on the day when measurement was conducted preceding today.

Thus, notification is given through personal number color 132, in a color different for each subject. Therefore, as personal number color 132 can visually be recognized from a position several meters away, the subject can be notified of which subject is urged to conduct measurement, in a recognizable manner.

If the biological information was measured one day before, the measurement time zone is a time zone including, for duration of one hour, thirty minutes before and after the time of measurement one day before. If the biological information was not measured one day before, the measurement time zone is a time zone including, for duration of one hour, thirty minutes before and after the time of measurement on the most recent day prior to one day before. In addition, if measurement is not conducted for three days, notification display control unit 114 does not have to give "notification" on the fourth day and later.

Here, as impedance of subject 20 varies within one day due to various physiological or environmental factors, the body composition varies depending on a condition at the time of measurement. In addition, as body composition monitor with scale 10 in the present embodiment measures the body composition only through lower limb, variation in a day is greater than when the body composition is measured through upper limb and lower limb. In order to check trend of daily variation by minimizing the influence of such circadian rhythm, the body composition is desirably measured at a fixed time every day.

In the present embodiment, as notification display control unit 114 notifies subject 20 that the current time is included in the time zone including, for duration of one hour, thirty minutes before and after the time of previous measurement, subject 20 can measure the biological information approximately at the same time of day every day. Consequently, the biological information suitable for observing trend of variation can be measured.

Though notification display control unit 114 gives notification through display in the present embodiment, the present invention is not limited as such and notification may be given by sound or motion such as vibration.

In addition, notification display control unit 114 may display frequency of measurement using ring mark 131 as described previously, together with notification with personal number color 132. Thus, not only subject 20 is urged to conduct measurement but also subject 20 can be notified of frequency of measurement, and therefore, subject 20 is further urged to conduct measurement of the biological information.

Figure 6:
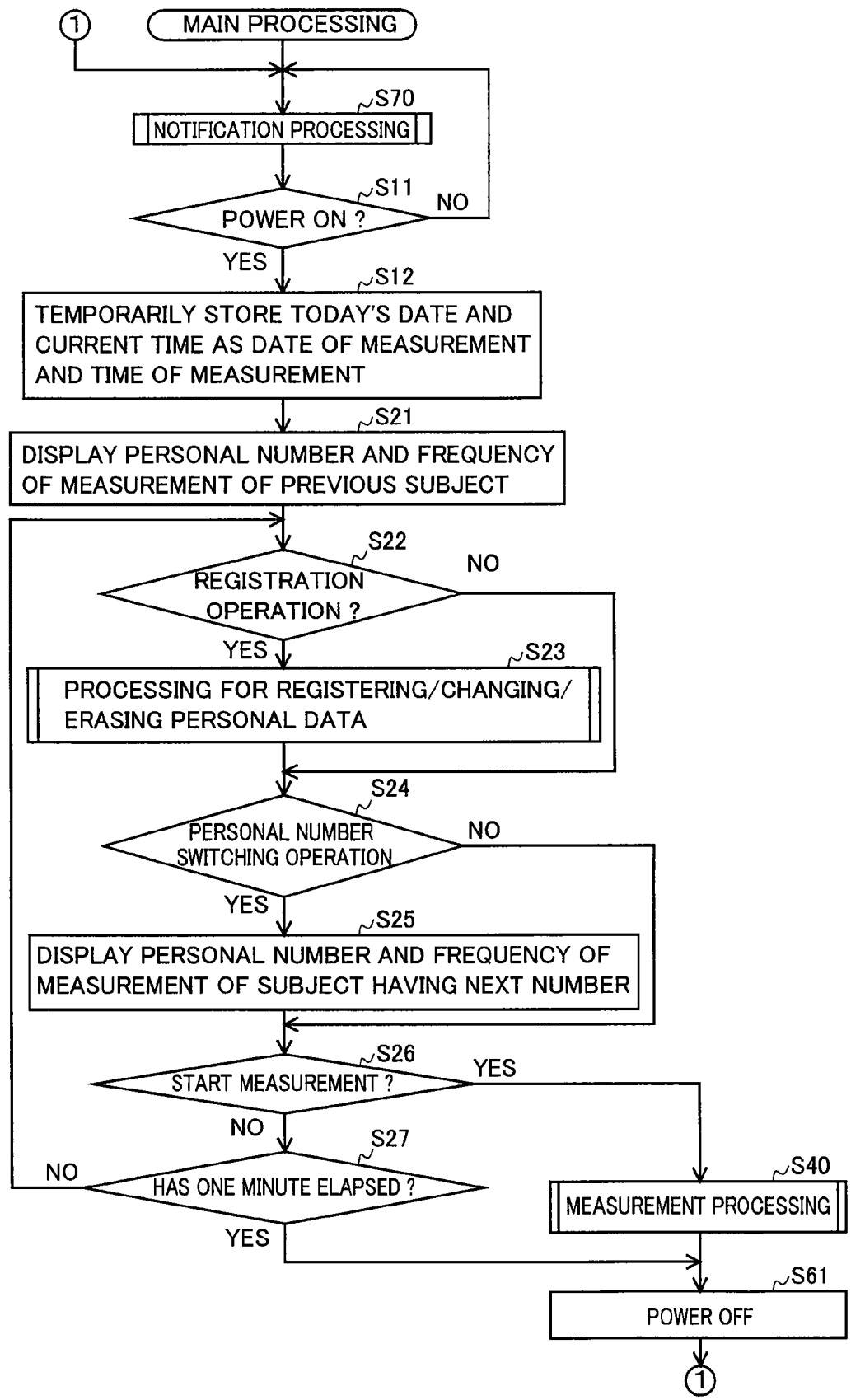
FIG. 6 is a flowchart showing a flow of main processing performed by the body composition monitor with scale in the present embodiment.

FIG. 6 is a flowchart showing a flow of main processing performed by body composition monitor with scale 10 in the present embodiment. Referring to FIG. 6, initially, in step S70, CPU 110 of body composition monitor with scale 10 performs notification processing. The notification processing will be described in connection with FIG. 10 later.

Thereafter, in step S11, CPU 110 determines whether subject 20 has operated ON switch 141 and turned on power. If CPU 110 determines that the power has not been turned on (NO in step S11), CPU 110 returns the processing to be performed to the processing in step S70.

On the other hand, if CPU 110 determines that the power has been turned on (YES in step S11), in step S12, CPU 110 causes the internal memory of CPU 110 to temporarily store today's date and current time as the date of measurement and time of measurement respectively.

Thereafter, in step S21, CPU 110 controls display unit 13 to display the personal number of the previous subject in the second row of display unit 13, "measurement record" and ring mark 131 showing frequency of measurement of the previous subject in the eighth row, "weight" in the third row, "0.0" with the segments in the fourth row, and "kg" in the fourth row. In addition, CPU 110 displays personal number color 132 in the eighth row in a color corresponding to the previous subject.

In next step S22, CPU 110 determines whether a registration operation for registering personal data has been performed through operation of operation unit 14 by subject 20. If CPU 110 determines that the registration operation has been performed (YES in step S22), in step S23, CPU 110 performs processing for registering/changing/erasing personal data.

The processing for registering/changing/erasing personal data refers to processing by each subject for setting and registering, changing, or erasing the personal data such as activation or inactivation of the notification function, height, sex, and date of birth.

If CPU 110 determines that the registration operation has not been performed (NO in step S22) or after step S23, in step S24, CPU 110 determines whether subject 20 has operated operation unit 14 to perform operation to switch the personal number.

If CPU 110 determines that the operation for switching the personal number has been performed (YES in step S24), in step S25, CPU 110 controls display unit 13 to display the personal number of the switched subject in the second row of display unit 13, "measurement record" and ring mark 131 showing frequency of measurement of the subject that has been switched to in the eighth row, "weight" in the third row, "0.0" with the segments in the fourth row, and "kg" in the fourth row. In addition, CPU 110 displays personal number color 132 in the eighth row in a color corresponding to the switched subject.

If CPU 110 determines that the operation for switching the personal number has not been performed (NO in step S24) or after step S25, in step S26, CPU 110 determines whether measurement has been started, by determining whether the weight information has been received from weight measurement unit 151 via input switching circuit 152 and A/D conversion circuit 153.

If CPU 110 determines that measurement has not been started (NO in step S26), in step S27, CPU 110 determines whether one minute has elapsed since the most recent operation out of the operation of ON switch 141, the operation in the processing for registering/changing/erasing personal data, and the operation for switching the personal number.

If CPU 110 determines that one minute has not elapsed since the most recent operation (NO in step S27), CPU 110 returns the processing to be performed to the processing in step S22. On the other hand, if CPU 110 determines that one minute has elapsed (YES in step S27), the processing to be performed proceeds to the processing in step S61.

On the other hand, when CPU 110 determines that the measurement has been started (YES in step S26), in step S40, CPU 110 performs measurement processing.

Figure 7:
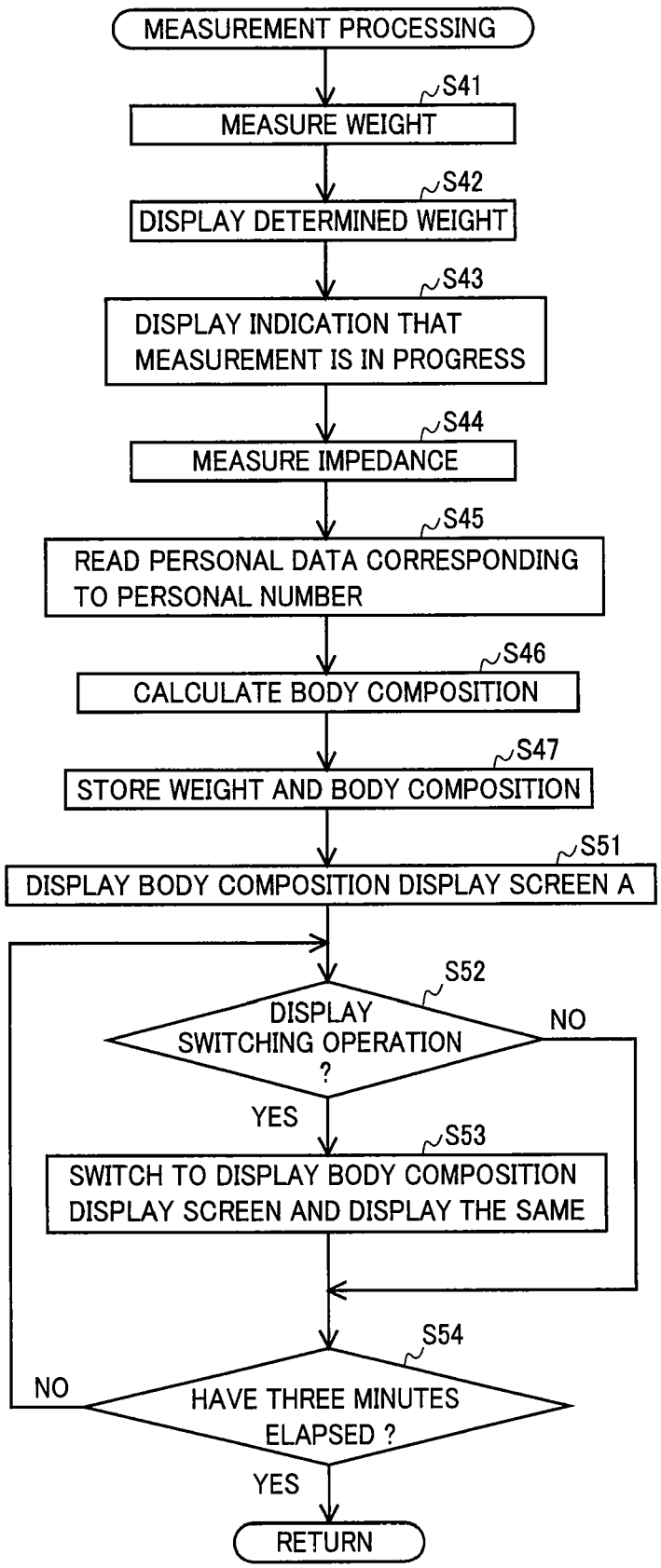
FIG. 7 is a flowchart showing a flow of measurement processing performed by the body composition monitor with scale in the present embodiment.

FIG. 7 is a flowchart showing a flow of measurement processing performed by body composition monitor with scale 10 in the present embodiment. Referring to FIG. 7, initially, in step S41, CPU 110 measures weight based on the received weight information.

Thereafter, in step S42, CPU 110 controls display unit 13 to display, for several seconds, the personal number of subject 20 in the second row of display unit 13, "weight" in the third row, the value of the weight that has been determined as a result of measurement in step S41 with the segments in the fourth row, and "kg" on the right thereof.

Thereafter, in step S43, CPU 110 controls display unit 13 to display "indication that measurement is in progress."

Figure 8:
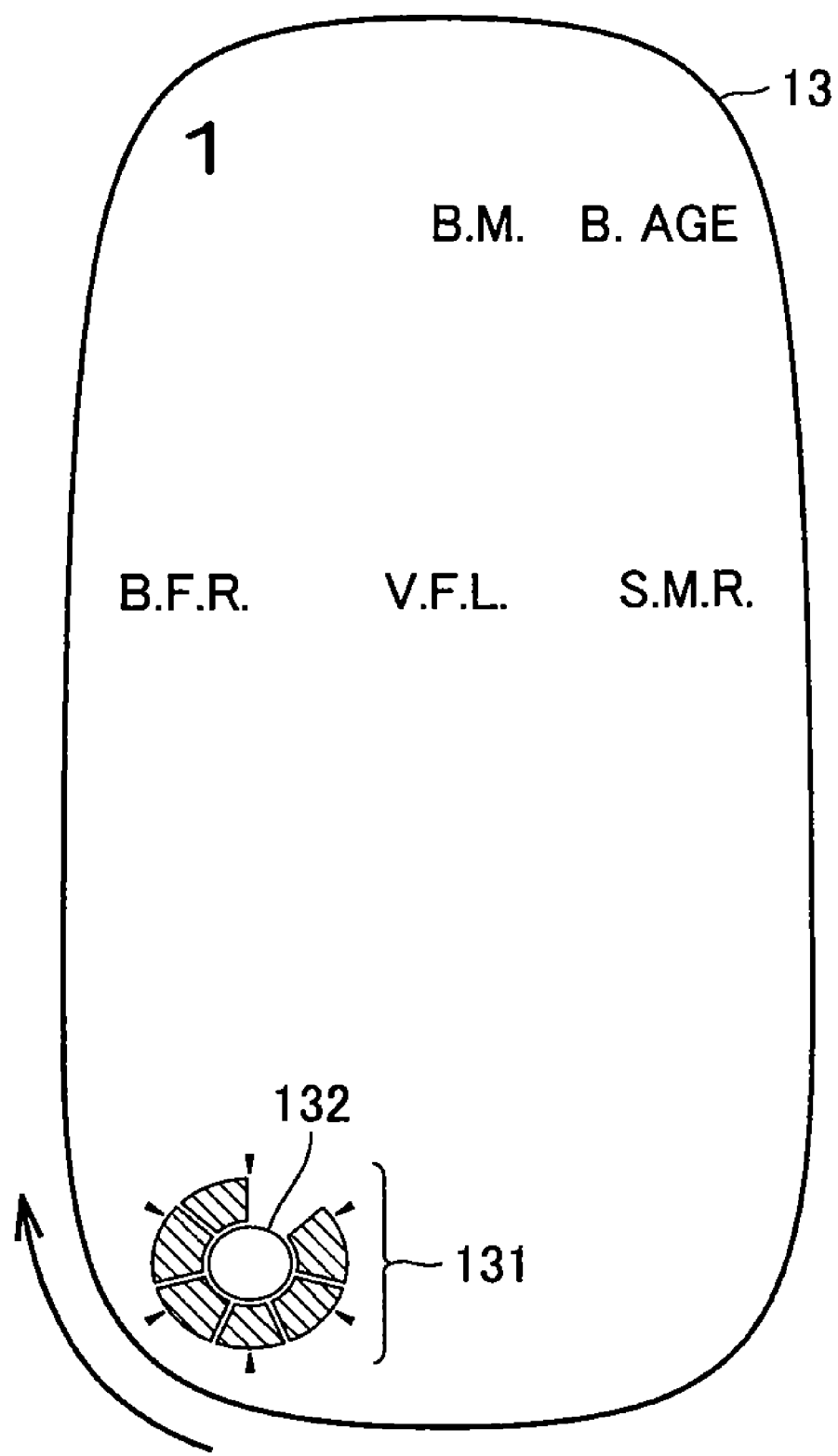
FIG. 8 is a display screen diagram showing indication that measurement is in progress, displayed on the display unit of the body composition monitor with scale in the present embodiment.

FIG. 8 is a display screen diagram showing indication that measurement is in progress displayed on display unit 13 of body composition monitor with scale 10 in the present embodiment. Referring to FIG. 8, the screen indicating that measurement is in progress displays the personal number of subject 20 in the second row of display unit 13, "basal metabolism" and "body age" in the third row, and "body fat rate", "visceral fat level" and "skeletal muscle rate" in the fifth row.

In addition, in the screen indicating that measurement is in progress, all blocks 133 to 139 in ring mark 131 are turned on. Then, blocks 133 to 139 are sequentially turned off, and the block that has been turned off is soon turned on again. Thus, ring mark 131 is displayed as if it were revolving, so that subject 20 is notified that body composition is being measured.

Referring back to FIG. 7, in step S44, CPU 110 measures impedance of subject 20 based on the voltage information received from voltage measurement electrodes 15C and 15D via input switching circuit 152 and the A/D conversion circuit.

Thereafter, in step S45, CPU 110 reads from memory 120, the height, sex and date of birth among personal data corresponding to the selected personal number.

Thereafter, in step S46, CPU 110 calculates the body composition of subject 20 based on the height, age and sex read in step S45, the weight measured in step S41, and impedance measured in step S44.

Thereafter, in step S47, CPU 110 causes memory 120 to store the date of measurement and the time of measurement provisionally stored in step S12 in the main processing, the weight measured in step S41, and the data of the body composition calculated in step S46, in a storage area corresponding to the number of days of "0" described with reference to Table 2.

As described previously, when the result of measurement is stored for the first time today, the data in the storage areas corresponding to the number of days from "0" through "96" is moved to the storage areas corresponding to the number of days of "1" through "97" and stored therein, respectively.

In next step S51, CPU 110 controls display unit 13 to display a "body composition display screen A."

Figure 9A:
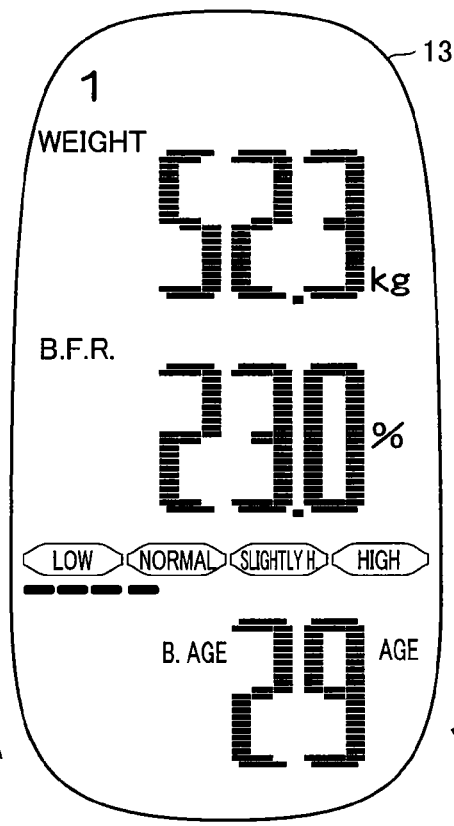
FIGS. 9A to 9C are display screen diagrams showing body composition display screens displayed on the display unit of the body composition monitor with scale in the present embodiment.
Figure 9C:
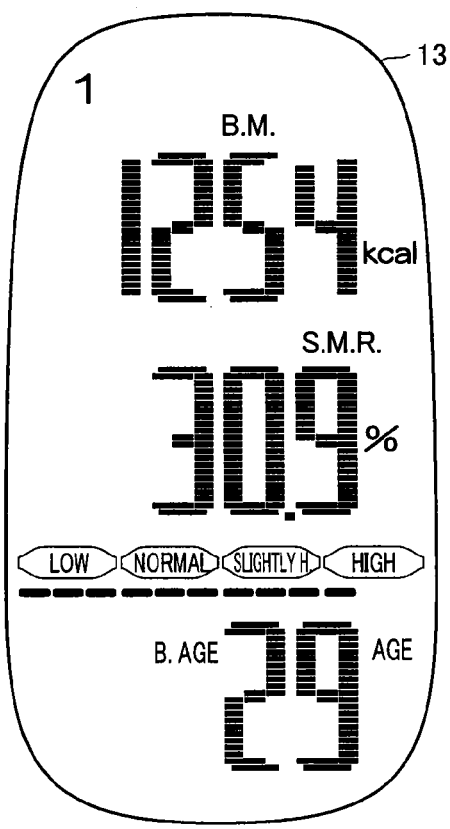
Figure 9B:
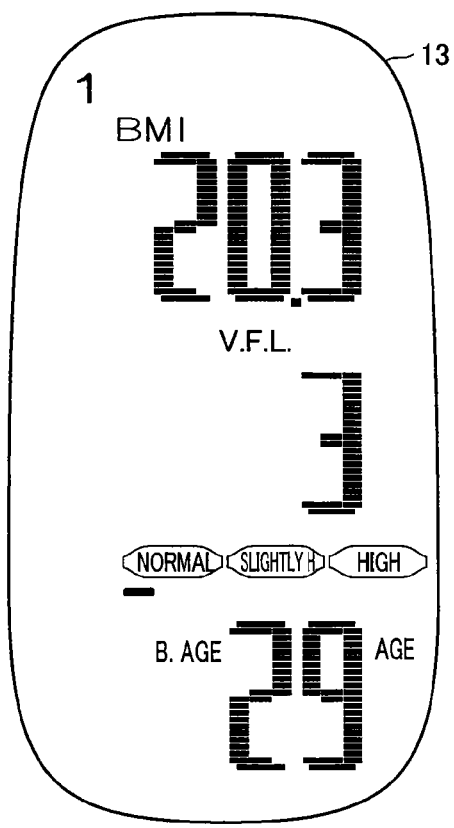

FIG. 9A to FIG. 9C are display screen diagrams showing body composition display screens displayed on display unit 13 of body composition monitor with scale 10 in the present embodiment.

Referring to FIG. 9A, body composition display screen A displays the personal number "1" of subject 20 in the second row, "weight" in the third row, "52.3" representing the value of weight, which is the result of measurement, with the segments in the fourth row, and "kg" representing the unit of weight on the right thereof. In addition, body composition display screen A displays "body fat rate" in the fifth row, "23.0" representing the value of the body fat rate, which is the result of calculation, with the segments in the sixth row, "%" representing the unit of the body fat rate on the right thereof, and a pictogram showing that the body fat rate level has been determined as the fourth level among twelve levels, that is, the "normal" level, in the seventh row. Moreover, body composition display screen A displays "body age" in the eighth row, "29" representing the value of the body age, which is the result of calculation, with the segments on the right thereof, and "age" representing the unit of the body age on the right thereof.

Referring back to FIG. 7, in step S52, CPU 110 determines whether the operation for switching display has been performed through operation of operation unit 14 by subject 20. If CPU 110 determines that the operation for switching display has been performed (YES in step S52), in step S53, CPU 110 controls display unit 13 to switch and display the body composition display screen.

Specifically, when the operation for switching display is performed while body composition display screen A is displayed, switching to a body composition display screen B is made and body composition display screen B is displayed. Similarly, when the operation for switching display is performed while body composition display screen B, C is displayed, switching to body composition display screen C, A is made and body composition display screen C, A is displayed.

Referring to FIG. 9B, body composition display screen B displays the personal number "1" of subject 20 in the second row, "BMI" in the third row, and "20.3" representing the value of BMI, which is the result of calculation, with the segments in the fourth row. In addition, body composition display screen B displays "visceral fat level" in the fifth row, "3" representing the value of the visceral fat level, which is the result of calculation, with the segments in the sixth row, and a pictogram showing that the visceral fat level has been determined as the first level among nine levels, that is, the "normal" level, in the seventh row. Moreover, body composition display screen B displays "body age" in the eighth row, "29" representing the value of the body age, which is the result of calculation, with the segments on the right thereof, and "age" representing the unit of the body age on the right thereof.

In addition, referring to FIG. 9C, body composition display screen C displays the personal number "1" of subject 20 in the second row, "basal metabolism" in the third row, "1254" representing the value of the basal metabolism, which is the result of calculation, with the segments in the fourth row, and "kcal" representing the unit of the basal metabolism on the right thereof. In addition, body composition display screen C displays "skeletal muscle rate" in the fifth row, "30.9" representing the value of the skeletal muscle rate, which is the result of calculation, with the segments in the sixth row, "%" representing the unit of the skeletal muscle rate on the right thereof, and a pictogram showing that the level of the skeletal muscle rate has been determined as the tenth level among twelve levels, that is, "high" level, in the seventh row. Moreover, body composition display screen C displays "body age" in the eighth row, "29" representing the value of the body age, which is the result of calculation, with the segment on the right thereof, and "age" representing the unit of the body age on the right thereof.

Referring back to FIG. 7, if CPU 110 determines that the operation for switching display has not been performed (NO in step S52) or after step S53, in step S54, CPU 110 determines whether three minutes have elapsed since last display of the body composition display screen. If CPU 110 determines that three minutes have not elapsed (NO in step S54), CPU 110 returns the processing to be performed to the processing in step S52.

On the other hand, if CPU 110 determines that three minutes have elapsed (YES in step S54), CPU 110 ends the measurement processing and returns the processing to be performed to the main processing.

Referring back to FIG. 6, after the measurement processing is performed in step S40 or when CPU 110 determines that one minute has elapsed since the most recent operation (YES in step S27), in step S61, CPU 110 controls power supply unit 170 to turn off power. Thereafter, CPU 110 returns the processing to be performed to the processing in step S70. As described previously, in step S70, CPU 110 performs notification processing.

Figure 10:
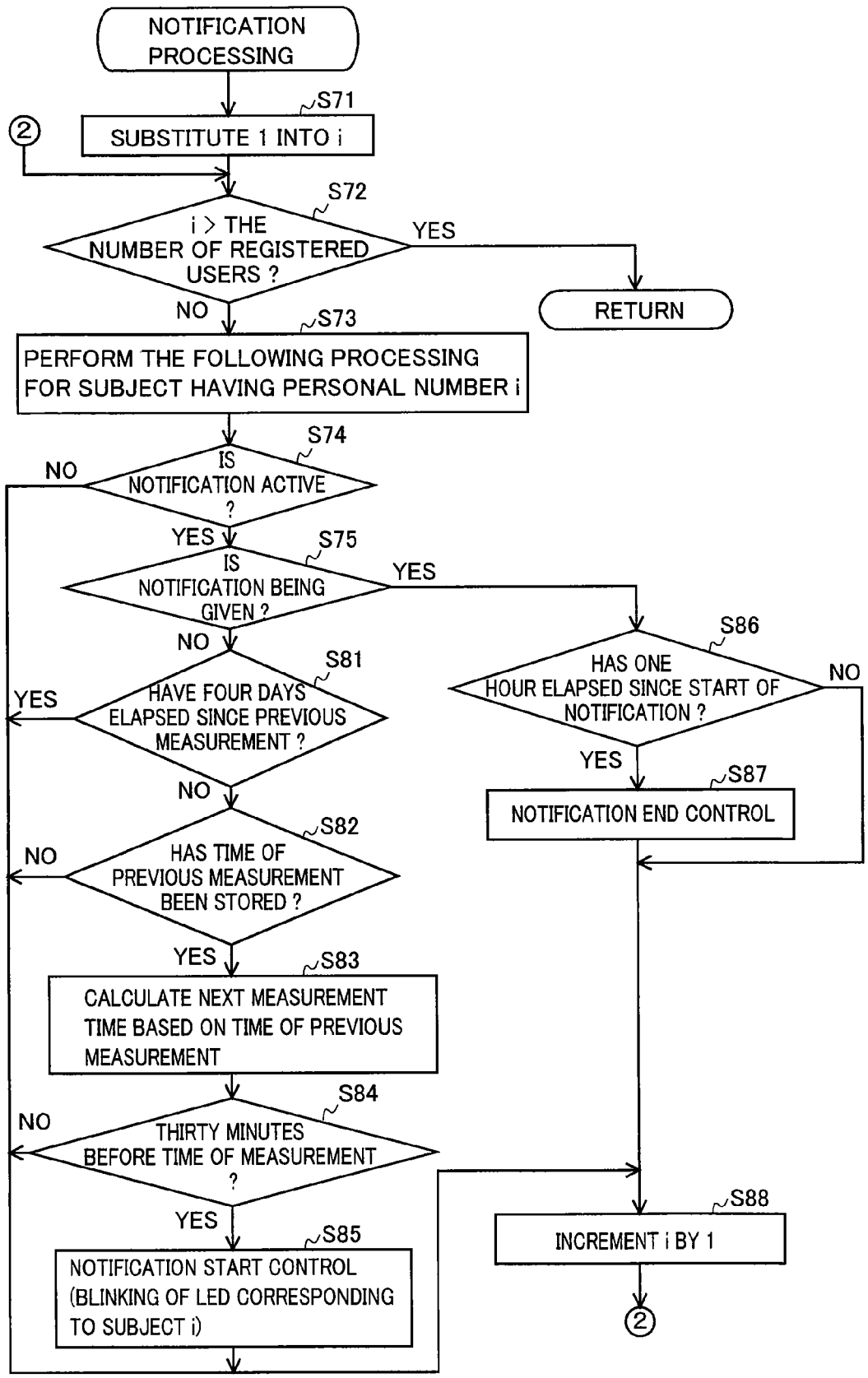
FIG. 10 is a flowchart showing a flow of notification processing performed by the body composition monitor with scale in the present embodiment.

FIG. 10 is a flowchart showing a flow of notification processing performed by body composition monitor with scale 10 in the present embodiment. Referring to FIG. 10, initially, in step S71, CPU 110 substitutes 1 into a variable i. Then, in step S72, CPU 110 determines whether variable i is greater than the number of registered users. For example, when the personal data as in Table 1 is stored in memory 120, the number of registered users is "3".

If CPU 110 determines that variable i is greater than the number of registered users (YES in step S72), CPU 110 ends the notification processing and returns the processing to be performed to the main processing. Namely, when the processing for all registered subjects ends, the processing to be performed returns to the main processing.

On the other hand, if CPU 110 determines that variable i is not greater than the number of registered users (NO in step S72), in step S73, setting is made such that the following processing is performed for the subject having personal number i.

In step S74, CPU 110 determines whether the notification function in the personal data for the subject having personal number i is on, that is, "active". If CPU 110 determines that "notification" is not "active", that is, the notification function is "off", i.e., "inactive" (NO in step S74), the processing to be performed proceeds to step S88.

On the other hand, if CPU 110 determines that "notification" is "active" (YES in step S74), in step S75, CPU 110 determines whether "notification" is being given for the subject having personal number i.

If CPU 110 determines that "notification" is not being given (NO in step S75), in step S81, CPU 110 determines whether four days have elapsed since previous measurement by the subject having personal number i. If CPU 110 determines that four days have elapsed (YES in step S81), the processing to be performed proceeds to the processing in step S88.

On the other hand, if CPU 110 determines that four days have not elapsed since the previous measurement (NO in step S81), in step S82, CPU 110 determines whether the time of measurement at which the subject having personal number i conducted measurement during a period from one day before to three days before has been stored in memory 120. The most recent time out of the times of measurement at which measurement was conducted during the period from one day before to three days before is assumed as the time of previous measurement.

For example, if the result of measurement by the subject having personal number i is stored as in Table 2, the time of measurement two days before is stored in memory 120 as the time of previous measurement. In addition, if body composition monitor with scale 10 is used for the first time or when memory 120 of body composition monitor with scale 10 is initialized, the time of previous measurement has not been stored in memory 120.

If CPU 110 determines that the time of previous measurement is not stored (NO in step S82), the processing to be performed proceeds to the processing in step S88. On the other hand, if CPU 110 determines that the time of previous measurement has been stored (YES in step S82), in step S83, CPU 110 calculates the time of present measurement based on the time of previous measurement. It is noted that the calculated time of measurement refers to the reference time of notification.

Specifically, 24 hours, 48 hours and 72 hours are added to combination of date and time of previous measurement (measurement date and time), to calculate three combinations of the date and time of measurement (hereinafter, referred to as "measurement notification date and time").

Thereafter, in step S84, CPU 110 determines whether combination of today's date and current time indicates thirty minutes before any of three measurement notification dates and times calculated in step S83.

In the present embodiment, in order to give "notification" every 24 hours, whether combination of today's date and current time indicates thirty minutes before the time 24 hours after, 48 hours after and 72 hours after the combination of the date and time of previous measurement is determined.

The present invention, however, is not limited as such. In order to give "notification" every 12 hours, whether combination of today's date and current time indicates thirty minutes before the time 12 hours after, 24 hours after, 36 hours after, 48 hours after, 60 hours after, and 72 hours after the combination of the date and time of previous measurement may be determined. Alternatively, another time interval such as every 8 hours instead of every 12 hours may be adopted.

In addition, in giving "notification" every 24 hours, whether four days have not elapsed since the day when previous measurement was conducted and whether the current time indicates thirty minutes before the time of previous measurement may be determined.

If CPU 110 determines that combination of today's date and current time does not indicate thirty minutes before any measurement notification date and time (NO in step S84), the processing to be performed proceeds to the processing in step S88.

On the other hand, if CPU 110 determines that combination of today's date and current time indicates thirty minutes before any measurement notification date and time (YES in step S84), in step S85, CPU 110 controls the three-color LED provided on the back side of display unit 13 so that personal number color 132 blinks in a color corresponding to the subject having personal number i, namely, to start "notification". Here, personal number color 132 blinks such that it is turned on every five seconds and turned off within one second. Thereafter, the processing to be performed proceeds to step S88.

If CPU 110 determines that "notification" is being given for the subject having personal number i (YES in step S75), in step S86, CPU 110 determines whether one hour has elapsed since the start of "notification". If CPU 110 determines that one hour has not elapsed (NO in step S86), the processing to be performed proceeds to step S88.

On the other hand, if CPU 110 determines that one hour has elapsed since the start of "notification" (YES in step S86), in step S87, CPU 110 controls the three-color LED to end blinking of personal number color 132 in the color corresponding to the subject having personal number i, namely, to end "notification". Thereafter, the processing to be performed proceeds to step S88.

In step S88, CPU 110 increments variable i by 1. Thereafter, the processing to be performed returns to the processing in step S72.

Figure 11:
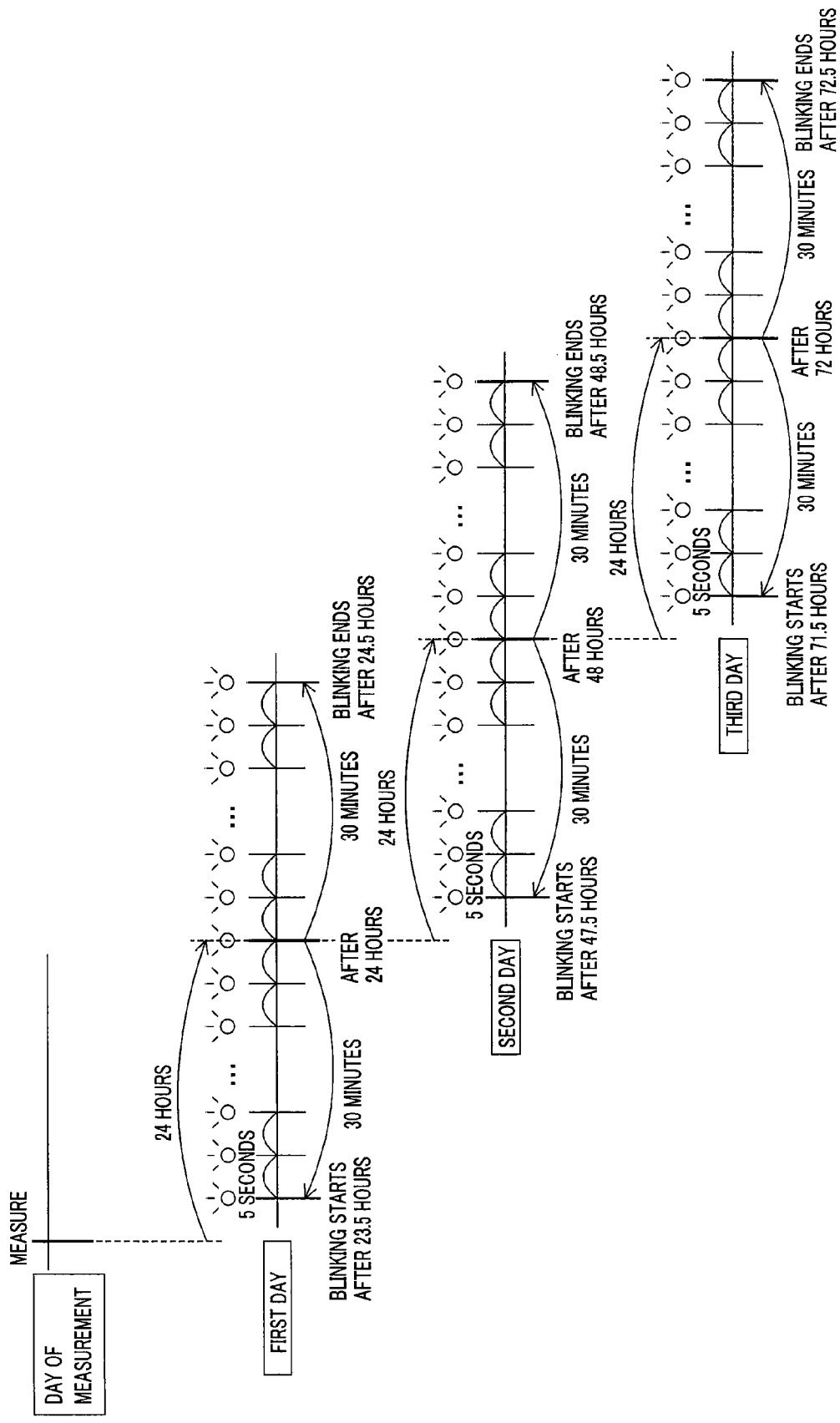
FIG. 11 is a timing chart of a notification function of the body composition monitor with scale in the present embodiment.

FIG. 11 is a timing chart of the notification function of body composition monitor with scale 10 in the present embodiment. Referring to FIG. 11, initially, on the first day from the last day of measurement, "notification" is given for duration of one hour, i.e., for thirty minutes before and after the time the same as the time of measurement on the last day of measurement (namely, 24 hours after). That is, personal number color 132 blinks in the color corresponding to the subject having personal number i.

Specifically, when the time thirty minutes before the time the same as the time of measurement on the last day of measurement comes on the day following the last day of measurement, (in other words, 23.5 hours after the time of measurement on the last day of measurement), "notification" is started. Then, when one hour has elapsed since the start of "notification" (in other words, 24.5 hours after the time of measurement on the last day of measurement), "notification" ends.

In the present embodiment, as described previously, personal number color 132 blinks such that it is turned on every five seconds and turned off within one second.

If the "notification" function for a plurality of subjects are set to "active", personal number color 132 is turned on in a color corresponding to the subject having the first personal number and the color is turned off within one second. Then, one second after turn-on of personal number color 132 in the color corresponding to the subject having the first personal number, personal number color 132 is turned on in a color corresponding to the subject having the next personal number and the color is turned off within one second. Such processing is repeated every fine seconds.

For the second day and the third day from the last day of measurement as well, "notification" is given for duration of one hour, i.e., for thirty minutes before and after the time the same as the time of measurement on the last day of measurement (namely, 48 hours after and 72 hours after). That is, personal number color 132 blinks in a color corresponding to the subject having personal number i. On the fourth day and later from the last day of measurement, "notification" is not given.

[First Variation]

Figure 12:
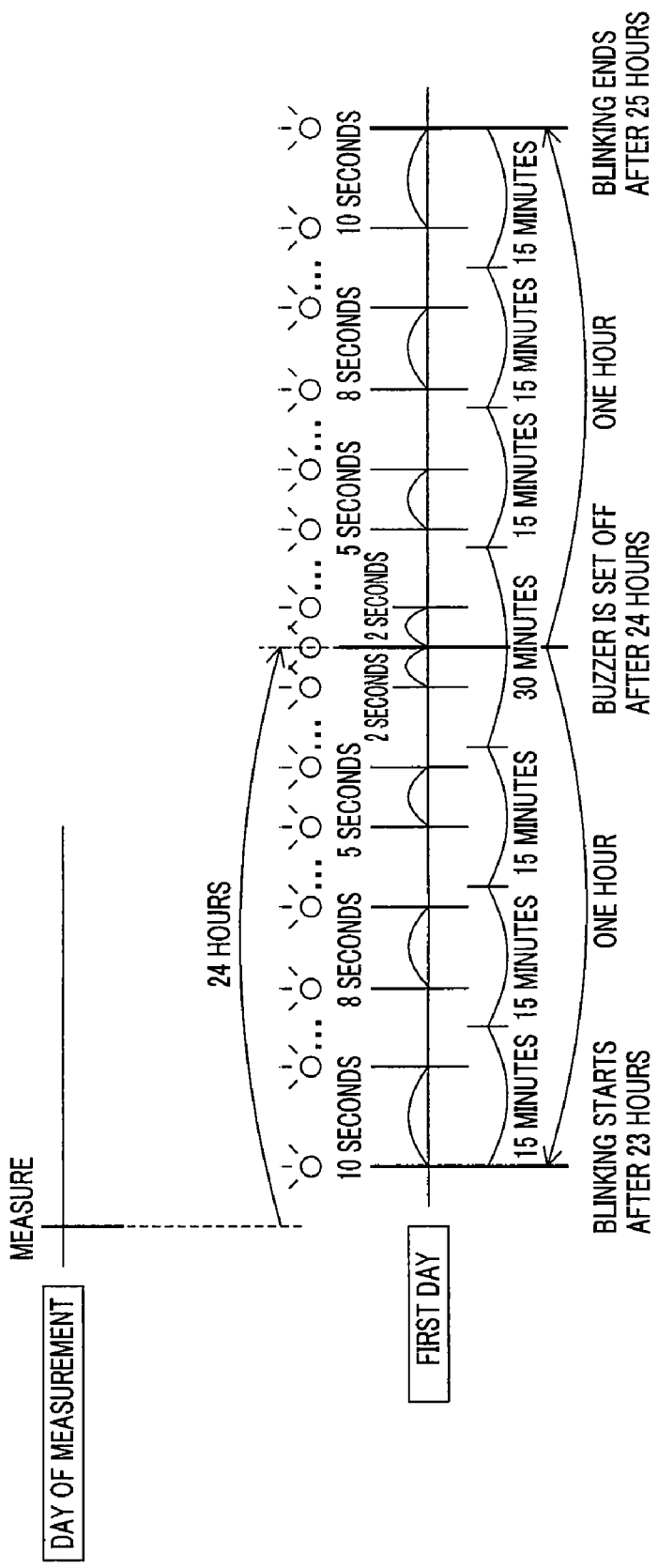
FIG. 12 is a timing chart of a notification function of the body composition monitor with scale in a first variation of the present embodiment.

FIG. 12 is a timing chart of the notification function of body composition monitor with scale 10 in a first variation of the present embodiment. In the embodiment described previously, on days first to third from the last day of measurement, "notification" is given for duration of one hour, i.e., for thirty minutes before and after the time the same as the time of measurement on the last day of measurement (namely, 24 hours after, 48 hours after and 72 hours after).

The present invention, however, is not limited as such, and referring to FIG. 12, "notification" may be given for duration of two hours, i.e., for one hour before and after the time the same as the time of measurement on the last day of measurement. Alternatively, notification may be given for a time period different from thirty minutes or one hour before and after the same.

In addition, in the embodiment described previously, personal number color 132 blinks at a constant interval of every five seconds. The present invention, however, is not limited as such, and during a prescribed period before and after point of time the same as the time of measurement on the last day of measurement, a blinking interval may be different, depending on a time from that point of time. Thus, the subject can be notified of the time from the point of time the same as the time of measurement on the last day of measurement.

For example, if "notification" is to be given for duration of two hours, i.e., for one hour before and after the time the same as the time of measurement on the last day of measurement, personal number color 132 is caused to blink every 10 seconds for a period from the time one hour before to the time 45 minutes before the time of measurement, every 8 seconds for a period from the time 45 minutes before to the time 30 minutes before the same, and every 5 seconds for a period from the time 30 minutes before to the time 15 minutes before the same. In addition, personal number color 132 is caused to blink every 2 seconds for a period from the time 15 minutes before to the time 15 minutes after the time of measurement, every 5 seconds for a period from the time 15 minutes after to the time 30 minutes after the same, every 8 seconds for a period from the time 30 minutes after to the time 45 minutes after the same, and every 10 seconds for a period from the time 45 minutes after to the time 60 minutes after the same.

Alternatively, a buzzer may be sounded at the time the same as the time of measurement on the last day of measurement. Thus, subject 20 can clearly be notified that the time the same as the time of measurement on the last day of measurement has come.

[Second Variation]

Figure 13:
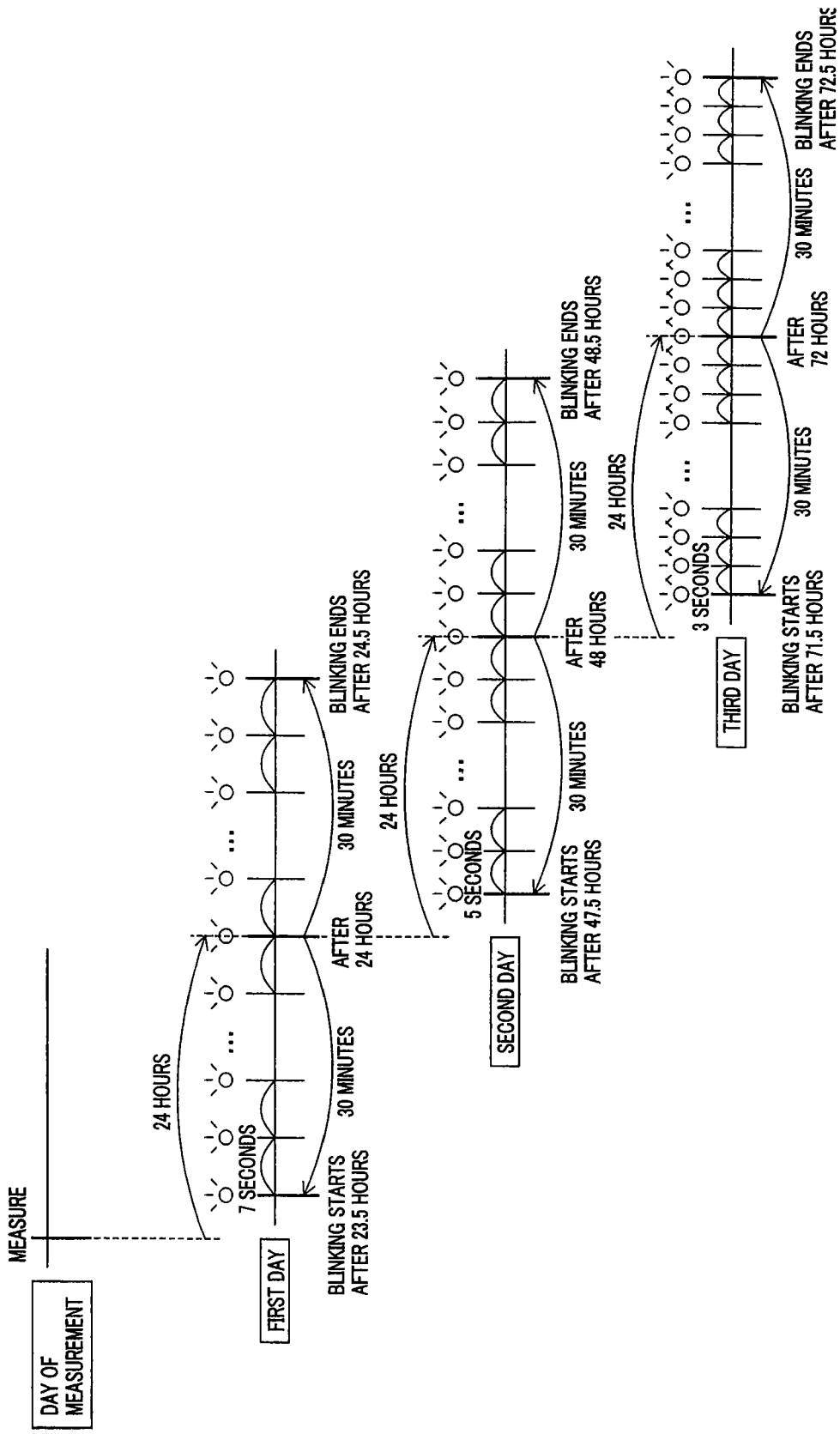
FIG. 13 is a timing chart of a notification function of the body composition monitor with scale in a second variation of the present embodiment.

FIG. 13 is a timing chart of the notification function of body composition monitor with scale 10 in a second variation of the present embodiment. In the embodiment described previously, on days first to third from the last day of measurement, personal number color 132 is caused to blink at a constant interval of every 5 seconds.

The present invention, however, is not limited as such, and referring to FIG. 13, the blinking interval may become shorter with lapse of day since the last day of measurement. Thus, subject 20 can more strongly be urged to conduct measurement with the lapse of day since the last day of measurement.

For example, personal number color 132 is caused to blink every 7 seconds on the first day from the last day of measurement, every 5 seconds on the second day, and every 3 seconds on the third day.

[Third Variation]

Figure 14:
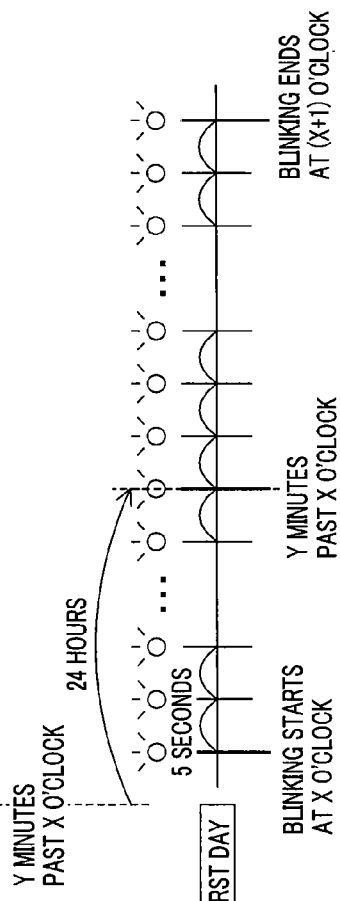
FIG. 14 is a timing chart of a notification function of the body composition monitor with scale in a third variation of the present embodiment.
Figure 14:
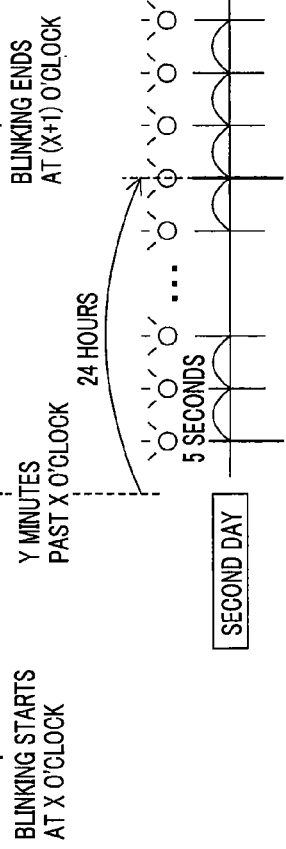
Figure 14:
Figure 14:
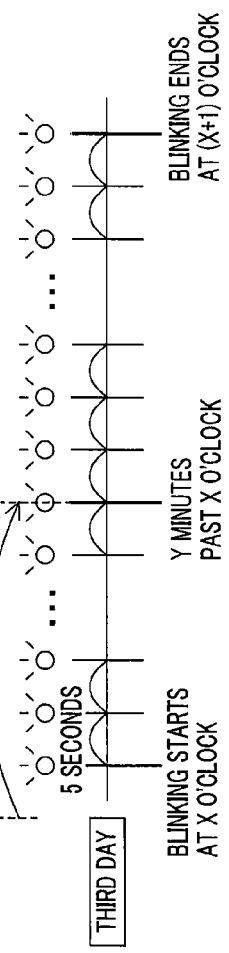
Figure 14:

FIG. 14 is a timing chart of the notification function of body composition monitor with scale 10 in a third variation of the present embodiment. In the embodiment described previously, on days first to third from the last day of measurement, "notification" is given for duration of one hour, i.e., for thirty minutes before and after the time the same as the time of measurement on the last day of measurement (namely, 24 hours after, 48 hours after and 72 hours after).

The present invention, however, is not limited as such, and referring to FIG. 14, when the time of measurement on the last day of measurement is assumed as Y minutes past X o'clock, on days first to third from the last day of measurement, "notification" may be given from 0 minutes past X o'clock until the time one hour after that.

For example, if the time of measurement on the last day of measurement is 45 minutes past 23 o'clock, in the embodiment described previously, "notification" is given from 15 minutes past 23 o'clock on that day to 15 minutes past 0 o'clock on the following day. Accordingly, if the subject measures the biological information during a period from 0 minutes past 0 o'clock to 15 minutes past 0 o'clock on the following day, it results in that measurement on that day (the preceding day) was not conducted, despite the fact that measurement was conducted in response to urge by the "notification".

In addition, in an example where the biological information is measured at 10 minutes past 0 o'clock, "notification" is given from 40 minutes past 23 o'clock on that day to 40 minutes past 0 o'clock on the following day. Here, if the subject measures the biological information during a period from 40 minutes past 23 o'clock to 59 minutes past 23 o'clock on that day, the result of measurement obtained at 40 minutes past 23 o'clock on that day overwrites the result of measurement obtained at 10 minutes past 0 o'clock on that day.

According to the manner as described above, for example, if the time of measurement on the last day of measurement is within a period from 23 o'clock until 0 o'clock, "notification" is given from 0 minutes past 23 o'clock on the following day until the time one hour after that. Alternatively, if the time of measurement on the last day of measurement is within a period from 0 o'clock until 1 o'clock, "notification" is given from 0 minutes past 0 o'clock on the following day until the time one hour after that.

Thus, setting can be made such that "notification" is not given across midnight. Therefore, such an event that a day when measurement was not conducted is produced or measurement is conducted twice on the same day, despite the fact that the biological information was measured in response to the "notification", can be avoided.

[Other Variations]

In the embodiment described previously, the invention of the body composition monitor with scale has been described, however, the present invention is not limited as such. Specifically, the present invention may be applied to a device with a function to measure weight being excluded from the body composition monitor with scale, namely, to a body composition monitor, or to a device with a function to measure body composition being excluded from the body composition monitor with scale, namely, to a scale.

Alternatively, in the embodiment described previously, the body composition monitor with scale for measuring body composition by feeding the current only to the lower limb has been described, however, the present invention is not limited as such. The present invention may be applied to a body composition monitor measuring body composition by feeding the current only to the upper limb, to a body composition monitor measuring body composition by feeding the current to both of the upper limb and the lower limb, or to a body composition monitor measuring body composition by feeding the current to a part other than the upper limb and the lower limb.

Alternatively, the present invention may be applied to a biological information measurement device regularly (for example, every day) measuring biological information, such as a blood pressure, body heat, blood glucose level, cholesterol in blood, and the like, without limited to body composition or weight.

Alternatively, in the embodiment described previously, "notification" is given by using the time of previous measurement as the reference, however, the present invention is not limited as such. Specifically, "notification" may be given by using a desired time of measurement set in advance by the subject as the reference.

Alternatively, in the embodiment described previously, the three-color LED has been used, however, the present invention is not limited as such, and other light-emitting devices such as a halogen lamp and an incandescent lamp may be employed.

Alternatively, in the embodiment described previously, a plurality of colors of light emitted by the three-color LED correspond to a plurality of subjects respectively. The present invention, however, is not limited as such, and a plurality of colors of light emitted by a plurality of single-color LEDs may correspond to a plurality of subjects respectively. Alternatively, a plurality of colors displayed by a color LCD may correspond to a plurality of subjects respectively.

Alternatively, in the embodiment described previously, one block of ring mark 131 is allotted to each day. The present invention, however, is not limited as such, and one block of ring mark 131 may be allotted to each week. For example, a block corresponding to a week during which measurement was conducted on three or more days may be turned on.

Alternatively, in the embodiment described previously, blocks 133 to 139 included in ring mark 131 are arranged on the circumference, however, the present invention is not limited as such. The blocks may be arranged on a line or on a side of a polygon.

Alternatively, in the embodiment described previously, the invention of body composition monitor with scale 10 has been described, however, the present invention is not limited as such. The present invention may be understood as the invention of a method of measuring biological information performing the processing in FIGS. 6, 7 and 10 in body composition monitor with scale 10.

Alternatively, the present invention may be understood as the invention of a biological information measurement program performing the processing in FIGS. 6, 7 and 10 in body composition monitor with scale 10 and a recording medium recording the biological information measurement program.

Although the present invention has been described and illustrated in detail, it is clearly understood that the same is by way of illustration and example only and is not to be taken by way of limitation, the scope of the present invention being limited only by the terms of the appended claims.

What is claimed is:

1. A biological information measurement device configured for measurement of biological data for a plurality of subjects, comprising:

a measurement unit for sensing characteristic information of a subject and converting the characteristic information to a corresponding signal;

a first calculation unit calculating biological information of said subject based on said corresponding signal;

a storage unit for storing, for each of the subjects, biological data representing data of said biological information calculated by said first calculation unit and measurement date data representing a day on which measurement by said measurement unit was conducted, in association with each other;

a time keeping unit performing a time keeping operation;

a display unit comprising a first area and a second area; and a display control unit carrying out, for each of the subjects, control for displaying measurement frequency specifying information in the first area of the display unit based on a plurality of pieces of said measurement date data stored in said storage unit and an output from said time keeping unit, the display control unit causing the second area of the display unit to emit light of a color predetermined for each subject so that the measurement frequency specifying information displayed in the first area of the display unit is identified by the color for each subject, wherein said measurement frequency specifying information specifies frequency of day(s) when said measurement was conducted in a past prescribed period from a current date.

2. The biological information measurement device according to claim 1, wherein said biological information includes at least any of weight and body composition.

3. The biological information measurement device according to claim 1, wherein said storage unit further stores measurement time data of said biological information in association with said biological data and said measurement date data, and said biological information measurement device further comprises a second calculation unit calculating next measurement time based on said measurement time data stored in said storage unit, and a notification unit performing processing for giving notification that current time is included in a prescribed time interval including said next measurement time calculated by said second calculation unit.

4. The biological information measurement device according to claim 3, wherein said prescribed time interval refers to a time interval starting from 0 minutes past X o'clock when said next measurement time is assumed as Y minutes past X o'clock.

5. The biological information measurement device according to claim 3, wherein said notification unit gives notification that said current time is included in said prescribed time interval through blinking of a light-emitting device or display and varies interval of turning on and blinking in accordance with a time from said next measurement time.

6. The biological information measurement device according to claim 3, wherein said notification unit gives notification that said current time is included in said prescribed time interval for the subject, by causing the second area to emit the light of the predetermined color using a light-emitting device or using a multiple color screen.

7. The biological information measurement device according to claim 3, wherein said display unit includes a liquid crystal panel, the first area comprises a plurality of blocks in the liquid crystal panel that corresponds to the number of days of the prescribed period and is arranged to surround the second area;

said display control unit displays said measurement frequency specifying information on said liquid crystal panel by displaying block(s) corresponding to the day(s) on which said measurement was conducted so as to distinguish the corresponding block(s) from other block(s), said biological information measurement device further comprises a light-emitting device provided on a back side of said liquid crystal panel and at a position corresponding to the second area such that light emitted therefrom is transmitted through said liquid crystal panel, and said notification unit gives notification that said current time is included in said prescribed time interval by turning on said light-emitting device and causing said light-emitting device to blink.

8. The biological information measurement device according to claim 7, wherein said light-emitting device is a multi-color LED, and said notification unit gives notification that said current time is included in said prescribed time interval for the subject, using a color of the light-emitting device predetermined for each said subject.

9. The biological information measurement device according to claim 1, wherein the first area comprises a plurality of blocks that corresponds to the number of days of the prescribed period, and said display control unit specifies number of days on which said measurement was conducted in said prescribed period, and displays said measurement frequency specifying information by displaying block(s) in number corresponding to said number of days on which said measurement was conducted so as to distinguish the corresponding block(s) from other block(s).

10. The biological information measurement device according to claim 1, wherein the first area comprises a plurality of blocks that corresponds to the number of days of the prescribed period and is arranged sequentially, and said display control unit displays said measurement frequency specifying information by displaying block(s) corresponding to the day(s) on which said measurement was conducted so as to distinguish the corresponding block(s) from other block(s).

11. The biological information measurement device according to claim 1, wherein said prescribed period is one week, the first area comprises seven blocks arranged sequentially and said display control unit displays said measurement frequency specifying information by displaying block(s) corresponding to the day(s) on which said measurement was conducted so as to distinguish the corresponding block(s) from other block(s).

12. A method of measuring biological information performed in a biological information measurement device, configured for measurement of biological data for a plurality of subjects, including a storage unit storing data, a display unit displaying data, a measurement unit for sensing characteristic information of a subject and converting the characteristic information to a corresponding signal, a time keeping unit performing a time keeping operation, and a control unit performing operation processing, comprising the steps of:

said control unit calculating biological information of said subject based on said corresponding signal;

said control unit causing said storage unit to store, for each subject, biological data representing data of calculated said biological information and measurement date data representing a day on which measurement by said measurement unit was conducted, in association with each other;

said control unit causing a first area of said display unit to display, for a subject, measurement frequency specifying information for specifying frequency of day(s) when said measurement was conducted in a past prescribed period from a current date, based on a plurality of pieces of said measurement date data stored in said storage unit and an output from said time keeping unit; and the display control unit causing a second area of the display unit to emit light of a color predetermined for the subject whose measurement frequency specifying information is displayed in the first area so as to identify the subject.

* * * * *